(12) United States Patent
Lee

(10) Patent No.: US 10,165,954 B2
(45) Date of Patent: Jan. 1, 2019

(54) INTEGRATED SENSOR MODULES

(71) Applicant: Salutron, Inc., Fremont, CA (US)

(72) Inventor: Yong Jin Lee, Seoul (KR)

(73) Assignee: SALUTRON INC., Newark, CA (US)

(*) Notice: Subject to any disclaimer, the term of this patent is extended or adjusted under 35 U.S.C. 154(b) by 486 days.

(21) Appl. No.: 14/661,819

(22) Filed: Mar. 18, 2015

(65) Prior Publication Data
US 2016/0029911 A1 Feb. 4, 2016

Related U.S. Application Data

(60) Provisional application No. 62/031,813, filed on Jul. 31, 2014, provisional application No. 62/058,492, filed on Oct. 1, 2014.

(51) Int. Cl.
*A61B 5/024* (2006.01)
*H01L 25/16* (2006.01)
(Continued)

(52) U.S. Cl.
CPC ........ *A61B 5/02427* (2013.01); *A61B 5/0205* (2013.01); *A61B 5/02416* (2013.01);
(Continued)

(58) Field of Classification Search
CPC .............. A61B 5/02427; A61B 5/0205; A61B 5/02416; A61B 5/0537; A61B 5/681;
(Continued)

(56) References Cited

U.S. PATENT DOCUMENTS 4,470,009 A * 9/1984 Takayanagi ............ G01R 29/24
324/457
5,473,949 A * 12/1995 Cage ..................... G01F 1/8409
73/32 A
(Continued)

OTHER PUBLICATIONS

Global Semiconductor Alliance, "Embedded Die Packaging Technologies Enable Innovative 2D and 3D Structures for Portable Applications", Innovator Update: Supplier Edition, vol. 21, No. 1, Mar. 2014.

*Primary Examiner* — Jessandra Hough
(74) *Attorney, Agent, or Firm* — Vierra Magen Marcus LLP

(57) ABSTRACT

An integrated sensor module includes one or more packaged light source semiconductor devices and one or more packaged light detector semiconductor devices mounted to a top surface of a substrate. A pre-molded cover structure includes a portion molded from an opaque molding compound and a further portion molded from a light transmissive molding compound. For each of the packaged light source and light detector semiconductor devices, the pre-molded cover structure includes a pre-molded cavity covered by a window formed of the light transmissive molding compound. The pre-molded cover structure is attached to the substrate such that each of the packaged light source and light detector semiconductor devices fits within a respective cavity, and such that a barrier formed of the opaque molding compound is positioned between each packaged light source semiconductor device and light detector semiconductor device. The module can also include additional sensors and/or electrodes for use by sensors.

19 Claims, 14 Drawing Sheets

(51) Int. Cl.
*A61B 5/00* (2006.01)
*A61B 5/0205* (2006.01)
*A61B 5/053* (2006.01)
*A61B 5/0245* (2006.01)

(52) U.S. Cl.
CPC ............ *A61B 5/0537* (2013.01); *A61B 5/681* (2013.01); *H01L 25/167* (2013.01); *A61B 5/0245* (2013.01); *A61B 5/0531* (2013.01); *H01L 2224/32245* (2013.01); *H01L 2224/48091* (2013.01); *H01L 2224/48247* (2013.01); *H01L 2224/73265* (2013.01)

(58) Field of Classification Search
CPC ... A61B 5/0245; A61B 5/0531; H01L 25/167; H01L 2224/32245; H01L 2224/48091; H01L 2224/48247; H01L 2224/73265
See application file for complete search history.

(56) References Cited

U.S. PATENT DOCUMENTS

| | | | |
|---|---|---|---|
| 5,678,544 A * | 10/1997 | DeLonzor | A61B 5/02427 351/41 |
| 6,420,818 B1 * | 7/2002 | Kishimoto | H04R 7/20 310/324 |
| 7,590,439 B2 * | 9/2009 | Raridan | A61B 5/14552 600/344 |
| 8,035,079 B2 | 10/2011 | Hane | |
| 8,677,605 B2 | 3/2014 | Lim et al. | |
| 9,136,236 B2 * | 9/2015 | Starkston | H01L 23/5385 |
| 9,392,946 B1 * | 7/2016 | Sarantos | A61B 5/14552 |
| 2006/0237540 A1 | 10/2006 | Saxena et al. | |
| 2010/0181578 A1 | 7/2010 | Li et al. | |
| 2010/0282951 A1 | 11/2010 | Costello et al. | |
| 2014/0021491 A1 * | 1/2014 | Meng | H01L 33/54 257/82 |
| 2014/0358012 A1 * | 12/2014 | Richards | A61B 5/02438 600/479 |
| 2015/0323360 A1 * | 11/2015 | Doi | G01F 1/692 73/204.26 |

* cited by examiner

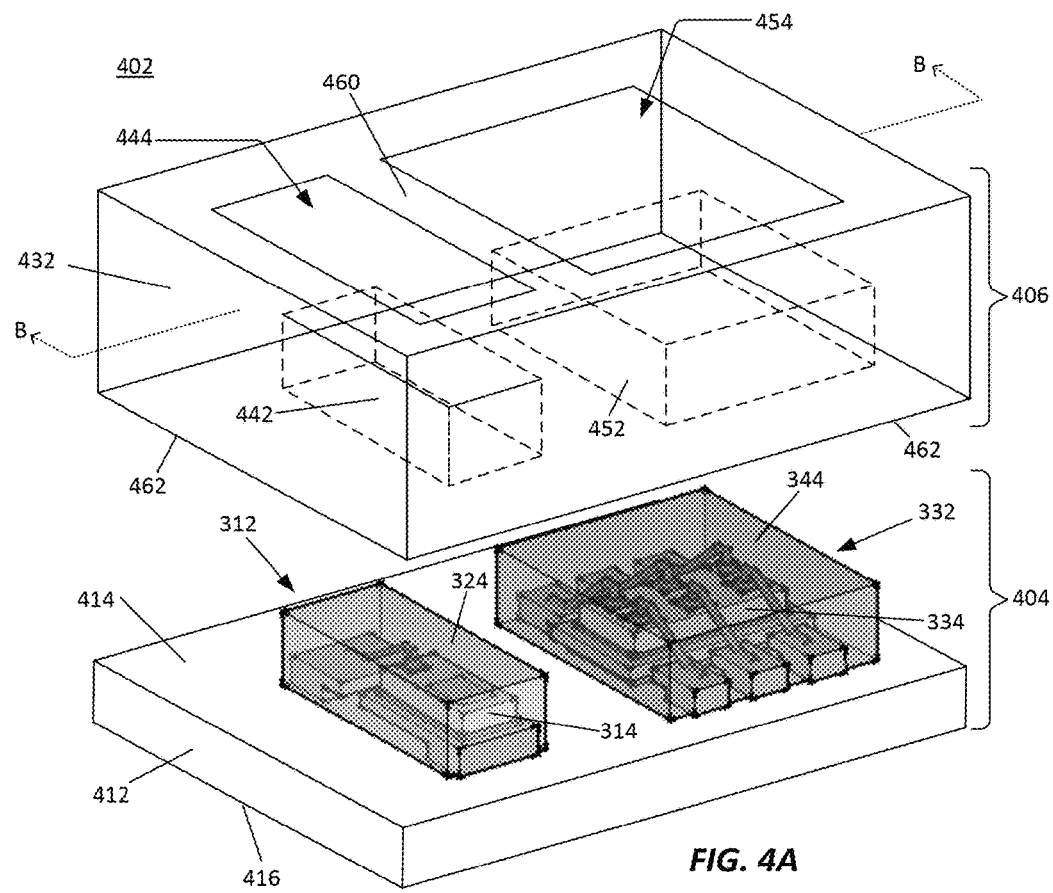
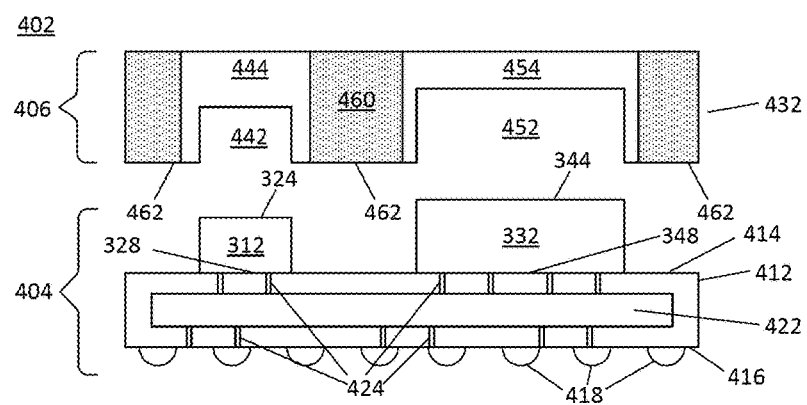

INTEGRATED SENSOR MODULES

PRIORITY CLAIM

This application claims priority to U.S. Provisional Patent Application No. 62/031,813, filed Jul. 31, 2014, and U.S. Provisional Patent Application No. 62/058,492, filed Oct. 1, 2014, each of which is incorporated herein by reference.

BACKGROUND

Sensors are being included in more and more products, including but not limited to user-wearable devices. For example, an optical sensor that includes a light source and a light detector may be included in a wrist-worn health and/or activity monitor, wherein the optical sensor operate as photoplethysmography (PPG) sensor that enables the wrist-worn monitor to measure heart rate (HR) and heart rate variability (HRV) of the person wearing the monitor on their wrist. For another example, an optical sensor may be included in a smart phone, wherein the optical sensor operates as a proximity sensor that can be used to determine when the phone is being held close to a persons' ear, in response to which a touchscreen of the phone is disabled so that functions are not accidently triggered if the person's ear touches the touchscreen. With such optical sensors, it is desirable to reduce and preferably minimize or eliminate optical crosstalk. Additionally, it is desirable that such optical sensors are compact, since they are often included in portable devices in which small size and light weight are preferred. Similarly, for other types of sensors it is typically desirable that they are compact, especially when included in portable devices.

BRIEF DESCRIPTION OF THE DRAWINGS

FIG. 4A is top perspective view of two subassemblies of an integrated sensor module, according to an embodiment of the present technology, before the two subassemblies are attached to one another.

FIG. 4B is a cross section of the two subassemblies shown in FIG. 4A.

DETAILED DESCRIPTION

Figures 1A, 1B:
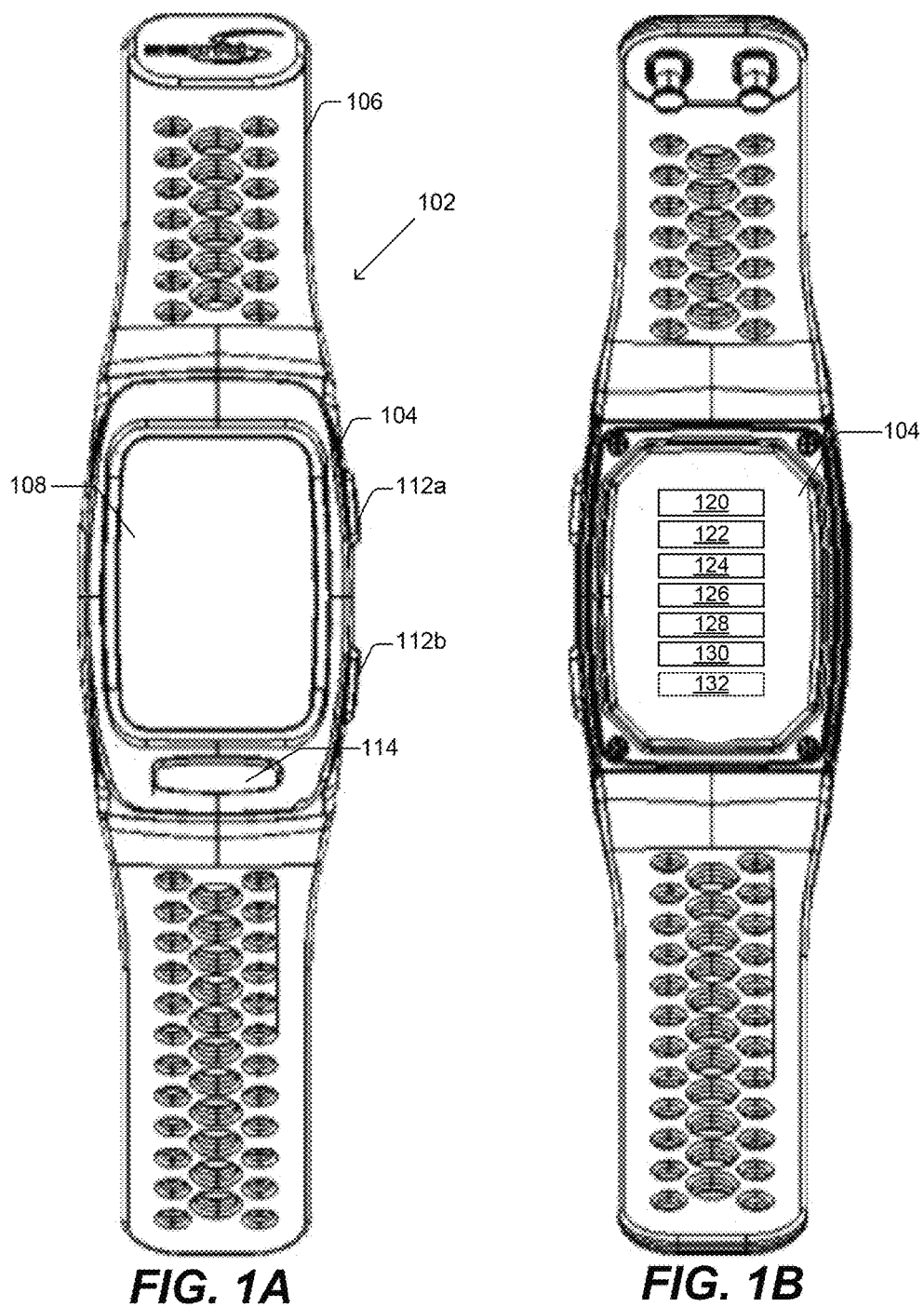
FIG. 1A depicts a front view of a user-wearable device, according to an embodiment.
FIG. 1B depicts a rear view of the user-wearable device of FIG. 1A, according to an embodiment.

In the following detailed description, reference is made to the accompanying drawings that form a part hereof, and in which is shown by way of illustration specific illustrative embodiments. It is to be understood that other embodiments may be utilized and that mechanical and electrical changes may be made. The following detailed description is, therefore, not to be taken in a limiting sense. In the description that follows, like numerals or reference designators will be used to refer to like parts or elements throughout. In addition, the first digit of a reference number identifies the drawing in which the reference number first appears.

Before describing integrated sensor modules of the present technology, it is first useful to describe an exemplary user-wearable device that can include an integrated sensor module. FIG. 1A depicts a front view of a user-wearable device 102, according to an embodiment. The user-wearable device 102 can be a standalone device which gathers and processes data and displays results to a user. Alternatively, the user-wearable device 102 can wirelessly communicate with a base station (252 in FIG. 2), which can be a mobile phone, a tablet computer, a personal data assistant (PDA), a laptop computer, a desktop computer, or some other computing device that is capable of performing wireless communication. The base station can, e.g., include a health and fitness software application and/or other applications, which can be referred to as apps. The user-wearable device 102 can upload data obtained by the device 102 to the base station, so that such data can be used by a health and fitness software application and/or other apps stored on and executed by the base station.

The user-wearable device 102 is shown as including a housing 104, which can also be referred to as a case 104. A band 106 is shown as being attached to the housing 104, wherein the band 106 can be used to strap the housing 104 to a user's wrist or arm. Where the user-wearable device 102 includes the wrist type band 106, the device 102 can also be referred to as a wrist-wearable or wrist-worn device. The band can alternatively be configured to strap the housing 104 to the user's chest so that sensors and/or electrodes (of or for use by the sensors) are in contact with the skin on the user's chest. A front side of the housing 104 is shown as including a digital display 108, which can also be referred to simply as a display. The digital display 108 can be used to show the time, date, day of the week and/or the like. The digital display 108 can also be used to display activity and/or physiological metrics, such as, but not limited to, heart rate (HR), heart rate variability (HRV), calories burned, steps taken and distance walked and/or run. The digital display 108 can also be used to display sleep metrics, examples of which are discussed below. Additionally, the digital display 108 can be used to display user notifications that inform a person wearing the user-wearable device to adjust their exposure to light. These are just a few examples of the types of information that may be displayed on the digital display 108, which are not intended to be all encompassing. As the terms are used herein, the terms user and person are used interchangeably.

The housing 104 is further shown as including buttons 112a, 112b, which can individually be referred to as a button 112, and can collectively be referred to as the buttons 112. One of the buttons 112 can be a mode select button, while another one of the buttons 112 can be used to start and stop certain features. While the user-wearable device 102 is shown as including two buttons 112, more or less than two buttons can be included. The buttons 112 can additionally or alternatively be used for other functions. The housing 104 is further shown as including a forward facing ECG electrode 114, which is discussed below. This ECG electrode 114 can also function as an additional button. While the shapes of the housing 104 and the digital display 108 are shown as generally being rectangular, they can alternatively have other shapes, such as, but not limited to, circular or oval shapes.

In certain embodiments, the user-wearable device 102 can receive alerts from a base station (e.g., 252 in FIG. 2), or can generate its own alerts. For example, where the base station 252 is a mobile phone, the user wearable device 100 can receive alerts from the base station, which can be displayed to the user on the display 108. For a more specific example, if a mobile phone type of base station 252 is receiving an incoming phone call, then an incoming phone call alert can be displayed on the digital display 108 of the mobile device, which may or may not include the phone number and/or identity of the caller. Other types of alerts include, e.g., text message alerts, social media alerts, calendar alerts, medication reminders and exercise reminders, but are not limited thereto. Still other types of alerts can inform a user that they should adjust their exposure to light, as will be described in additional detail below. Such alerts can be generated solely by the user-wearable device 102, or with the assistance of a base station (e.g., 252) with which the user-wearable device 102 wirelessly communicates. The user-wearable device 102 can inform the user of a new alert by vibrating and/or emitting an audible sound.

FIG. 1B illustrates an exemplary rear-view of the housing or case 104 of the user-wearable device 102. Referring to FIG. 1B, the backside of the housing 104, which can also be referred to as a caseback, is schematically shown as including a bioimpedance analysis (BIA) sensor, an optical sensor 122, a capacitive sensor 124, a galvanic skin resistance (GSR) sensor 126, an electrocardiogram (ECG) sensor 128 and a skin temperature sensor 130. It is also possible that the user-wearable device 102 includes less sensors than shown, more sensors than shown and/or alternative types of sensors. For example, the user-wearable device 102 can also include one or more type of motion sensor 132, which is shown in dotted line because it is likely completely encased with the housing 104.

In accordance with an embodiment, the bioimpedance analysis (BIA) sensor 120, which can include or connect to a pair of electrodes spaced apart from one another such that a patient's skin can complete a circuit between the electrodes, passes a current at a single frequency, or more preferably at multiple frequencies, through a user's tissue (proximate the sensor electrodes) and measures impedance. Based on these impedance measurements, algorithms, linear regression models and/or other mathematical modeling can be used to calculate the user's body water content and/or body fat percentage.

In accordance with an embodiment, the optical sensor 122 includes both a light source and a light detector, in which case the optical sensor 122 can be used to detect proximity of an object (e.g., a user's wrist or chest) relative to the optical sensor, as well as to detect ambient light. The light source of the optical sensor 122 can include one or more light emitting diode (LED), incandescent lamp or laser diode, but is not limited thereto. While infrared (IR) light sources are often employed in optical sensors, because the human eye cannot detect IR light, the light source can alternatively produce light of other wavelengths. The light detector of the optical sensor 122 can include one or more one or more photoresistor, photodiode, phototransistor, photodarlington or avalanche photodiode, but is not limited thereto. When operating as an optical proximity sensor, the light source of the optical sensor 122 is driven to emit light. If an object (e.g., a user's wrist or chest) is within the sense region of the optical sensor 122, a large portion of the light emitted by the light source will be reflected off the object and will be incident on the light detector. The light detector generates a signal (e.g., a current) that is indicative of the intensity and/or phase of the light incident on the light detector, and thus, can be used to detect the presence of the user's wrist or chest. The optical sensor 122 may also use its light detector to operate as an ambient light detector. It is also possible that the optical sensor 122 not include a light source, in which case the optical sensor 122 can operate as an ambient light sensor, but not a proximity sensor. When operating as an ambient light sensor, the optical sensor 122 produces a signal having a magnitude that is dependent on the amount of ambient light that is incident on the optical sensor 122. It is expected that when a user is wearing the user-wearable device 102 on their wrist or chest, the light detector of the optical sensor 122 will be blocked (by the user's wrist or chest) from detecting ambient light, and thus, the signal produced the light detector will have a very low magnitude.

In accordance with specific embodiments, the optical sensor 122 can also be used to detect heart rate (HR) and heart rate variability (HRV). More specifically, the optical sensor 122 can operate as a photoplethysmography (PPG) sensor. When operating as a PPG sensor, the light source of the optical sensor 122 emits light that is reflected or back-scattered by patient tissue, and reflected/backscattered light is received by the light detector of the optical sensor 122. In this manner, changes in reflected light intensity are detected by the light detector, which outputs a PPG signal indicative of the changes in detected light, which are indicative of changes in blood volume. The PPG signal output by the light detector can be filtered and amplified, and can be converted to a digital signal using an analog-to-digital converter (ADC), if the PPG signal is to be analyzed in the digital domain. Each cardiac cycle in the PPG signal generally appears as a peak, thereby enabling the PPG signal to be used to detect peak-to-peak intervals, which can be used to calculate heart rate (HR) and heart rate variability (HRV). In accordance with certain embodiments, described below, a PPG signal sensed using the optical sensor 122 is used to determine whether or not to authenticate a user. In accordance with certain embodiments, the optical sensor 122 includes a light source that emits light of two different wavelengths that enables the optical sensor 122 to be used as a pulse oximeter, in which case the optical sensor 122 can non-invasively monitor the arterial oxygen saturation of a user wearing the user-wearable device 102.

In accordance with an embodiment, the capacitive sensor 124 includes or connects to an electrode that functions as one plate of a capacitor, while an object (e.g., a user's wrist or chest) that is in close proximity to the capacitive sensor 124 functions as the other plate of the capacitor. The capacitive sensor 124 can indirectly measure capacitance, and thus proximity, e.g., by adjusting the frequency of an oscillator in dependence on the proximity of an object relative to the capacitive sensor 124, or by varying the level of coupling or attenuation of an AC signal in dependence on the proximity of an object relative to the capacitive sensor 124.

The galvanic skin resistance (GSR) sensor 126, which can include or connect to a pair of electrodes spaced apart from one another such that a patient's skin can complete a circuit between the electrodes, senses a galvanic skin resistance. The galvanic skin resistance measurement will be relatively low when a user is wearing the user-wearable device 102 on their wrist or chest and the GSR sensor 126 is in contact with the user's skin. By contrast, the galvanic skin resistance measurement will be very high when a user is not wearing the user-wearable device 102 and the GSR sensor 126 is not in contact with the user's skin. The galvanic skin resistance measurement, which can also be referred to as a galvanic skin response, may also vary based on levels perspiration.

The ECG sensor 128 can be used to sense an ECG signal from a user that is wearing the user-wearable device 102 on their wrist or chest. If the user-wearable device 102 is worn on the user's wrist, then an ECG signal can be sensed when an electrode on the caseback of the housing 104 is in contact with the skin on the user's wrist, and the user's touches the forward facing electrode 114 using a finger on their other arm. If the user-wearable device 102 is worn on the user's chest, then an ECG signal can be sensed between two electrodes on the back of the housing 104 that are in contact with the skin on the user's chest.

The skin temperature sensor 130 can be implemented, e.g., using a thermistor, and can be used to sense the temperature of a user's skin, which can be used to determine user activity and/or calories burned.

Depending upon implementation, heart rate (HR) and heart rate variability (HRV) can be detected based on signals obtained by the optical sensor 122 and/or the ECG sensor 128. HR and/or HRV can be automatically determined continuously, periodically or at other specified times or based on a manual user action. For example, in a free living application, HR can be determined automatically during periods of interest, such as when a significant amount of activity is detected.

Additional physiologic metrics can also be obtained using the sensors described herein. For example, respiration rate can be determined from a PPG signal obtained using the optical sensor 122 and/or from the ECG signal determined using the ECG sensor 128. For another example, blood pressure can be determined from PPG and ECG signals by determining a metric of pulse wave velocity (PWV) and converting the metric of PWV to a metric of blood pressure. More specifically, a metric of PWV can be determining by determining a time from a specific feature (e.g., an R-wave) of an obtained ECG signal to a specific feature (e.g., a maximum upward slope, a maximum peak or a dicrotic notch) of a simultaneously obtained PPG signal. An equation can then be used to convert the metric of PWV to a metric of blood pressure.

In accordance with an embodiment the motion sensor 132 is an accelerometer. The accelerometer can be a three-axis accelerometer, which is also known as a three-dimensional (3D) accelerometer, but is not limited thereto. The accelerometer may provide an analog output signal representing acceleration in one or more directions. For example, the accelerometer can provide a measure of acceleration with respect to x, y and z axes. The motion sensor 132 can alternatively be a gyrometer, which provides a measure of angular velocity with respect to x, y and z axes. It is also possible that the motion sensor 132 is an inclinometer, which provides a measure of pitch, roll and yaw that correspond to rotation angles around x, y and z axes. It is also possible the user wearable device 102 includes multiple different types of motion sensors, some examples of which were just described. Depending upon the type(s) of motion sensor(s) used, such a sensor can be used to detect the posture of a portion of a user's body (e.g., a wrist or chest) on which the user-wearable device 102 is being worn.

Figure 1C:
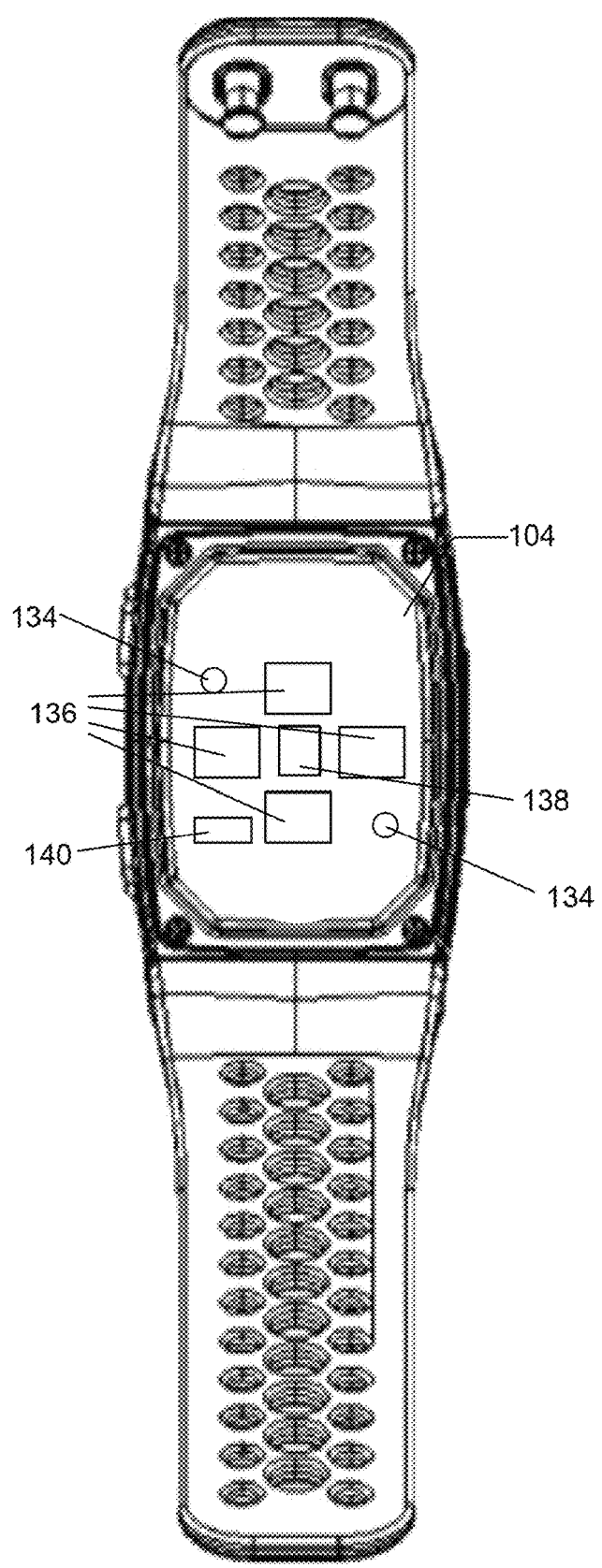
FIG. 1C depicts a specific implementation of contact sensors that are viewable from the rear or caseback of the user-wearable device of FIGS. 1A and 1B, according to an embodiment.

In the specific embodiments illustrated in FIGS. 1A, 1B and 1C the user-wearable device 102 is intended to be worn on a wrist, and thus, can be referred to as a wrist wearable device 102. FIG. 1C illustrates a rear-view of the housing or case 104 of the user-wearable device 102 according to a specific embodiment. Referring to FIG. 1C, the back of the housing or case 104, which can also be referred to as the caseback, is shown as including two electrodes or electrode contacts 134 that are spaced apart from one another, four light emitting devices 136, a light detecting device 138, and a metal temperature sensor contact 140.

In accordance with an embodiment, the light emitting devices 136 and the light detecting device 138 are components of the optical sensor 122 that was discussed above. The optical sensor 122 can alternatively include as few as one light emitting device, two or three light emitting devices, or more than four light emitting device. It is also possible that the optical sensor 122 includes multiple light detecting devices 138. The light emitting device(s) and light detecting device(s) of the optical sensor 122 are likely covered by light transmissive windows that protect the light emitting device(s) and light detecting device(s).

The two electrodes 134 and 134 can be used for the BIA sensor 120, the capacitive sensor 124, the GSR sensor 126 and the/or ECG sensor 128. For example, switches (not shown) can be used to selectively connect the electrodes 134 to various different electrical circuits within the housing 104 so that they can selectively function as parts of different types of sensors. More specifically, such switches can selectively connected to the two electrodes 134 to either BIA sensor circuitry, capacitive sensor circuitry, GSR sensor circuitry or ECG sensor circuitry. Where electrode(s) that are used by the BIA sensor 120, the capacitive sensor 124, the GSR sensor 126 and the/or ECG sensor 128 are in contact with the user's skin, such sensors are considered to be in contact with the user's skin.

Figure 2:
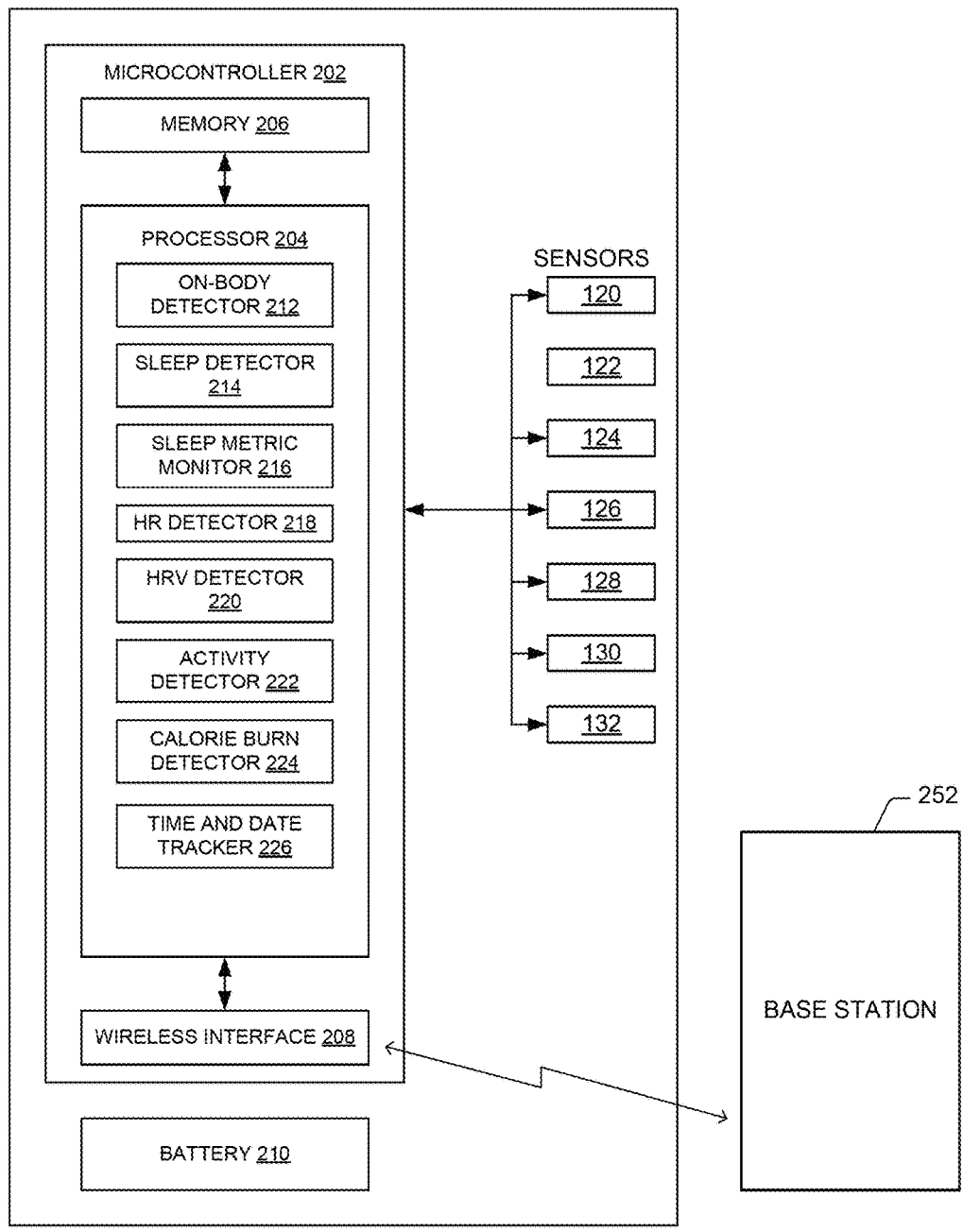
FIG. 2 depicts a high level block diagram of electrical components of the user-wearable device introduced in FIGS. 1A, 1B and 1C, according to an embodiment.

Each of the aforementioned sensors 122, 124, 126, 128, 130, 132 can include or have associated analog signal processing circuitry to amplify and/or filter raw signals produced by the sensors. It is also noted that analog signals produced using the aforementioned sensors 122, 124, 126, 128, 130 and 122 can be converted to digital signals using one or more digital to analog converters (ADCs), as is known in the art. The analog or digital signals produced using these sensors can be subject time domain processing, or can be converted to the frequency domain (e.g., using a Fast Fourier Transform or Discrete Fourier Transform) and subject to frequency domain processing. Such time domain processing, frequency domain conversion and/or frequency domain processing can be performed by a processor (e.g., 204), or by some other circuitry. FIG. 2 depicts an example block diagram of electrical components of the user-wearable device 102, according to an embodiment. Referring to FIG. 2, the user-wearable device 102 is shown as including a microcontroller 202 that includes a processor 204, memory 206 and a wireless interface 208. It is also possible that the memory 206 and wireless interface 208, or portions thereof, are external the microcontroller 202. The microcontroller 202 is shown as receiving signals from each of the aforementioned sensors 122, 130 and 132. The user-wearable device 102 is also shown as including a battery 210 that is used to power the various components of the device 102. While not specifically shown, the user-wearable device 102 can also include one or more voltage regulators that are used to step-up and or step-down the voltage provided by the battery 210 to appropriate levels to power the various components of the device 102.

Each of the aforementioned sensors 120, 122, 124, 126, 128, 130, 132 can also include its own circuitry to obtain signals of interest and/or information indicative thereof. For example, the BIA sensor 120 can include circuitry that enables impedance to be measured between a pair of electrodes in contact with a user's skin at one or more frequencies. The optical sensor 122 can include circuitry that selectively drives the light source of the optical sensor 122 and circuitry that amplifies and/or filters a signal produced by the light detector of the optical sensor 122, and/or converts a current signal produced by the light detector to a voltage signal. The GSR sensor 126 can include circuitry that senses a galvanic skin resistance between a pair of electrode in contact with a user's skin. For another example, the ECG sensor 128 can include circuitry that enables an ECG signal to be sensed between a pair of electrodes in contact with a user's skin. Each of the sensors that requires that one or more electrodes be in contact with a user's skin can include or be coupled to electrodes that are dedicated to the sensor. Alternatively, two or more of the sensors that require one or more electrodes be in contact with a user's skin can share common electrodes, e.g., using switches that selectively connect electrodes to appropriate sensor circuitry in a time divisional multiplexed manner. For a more specific example, there can be a total of two electrodes (e.g., 134) on the backside of the housing 104 that contact a user's skin when the device 102 is being worn by the user. Where a sensor only requires a single electrode on the backside of the housing 104, one of the two electrodes can be used, or the two electrodes can be electrically coupled together to function as a single electrode having a larger surface area than an individual electrode. Additionally, where the battery (e.g., 210) of the device is a rechargeable battery, the same two electrodes on the backside of the housing 104 can also be selectively used to charge the battery.

The wireless interface 208 can wireless communicate with a base station (e.g., 252), which as mentioned above, can be a mobile phone, a tablet computer, a PDA, a laptop computer, a desktop computer, or some other computing device that is capable of performing wireless communication. The wireless interface 208, and more generally the user wearable device 102, can communicate with a base station 252 using various different protocols and technologies, such as, but not limited to, Bluetooth™, Wi-Fi, ZigBee or ultra-wideband (UWB) communication. In accordance with an embodiment, the wireless interface 208 comprises telemetry circuitry that include a radio frequency (RF) transceiver electrically connected to an antenna (not shown), e.g., by a coaxial cable or other transmission line. Such an RF transceiver can include, e.g., any well-known circuitry for transmitting and receiving RF signals via an antenna to and from an RF transceiver of a base station 252.

The user-wearable device 102 is shown as including various detectors or trackers, including an on-body detector 212, a sleep detector 214, a sleep metric detector 216, a heart rate (HR) detector 218, a heart rate variability (HRV) detector 220, an activity detector 222, a calorie burn detector 224 and a time and date tracker 226. The various detectors and trackers may communicate with one another, as will be explained below. Each of these detectors and trackers 212, 214, 216, 218, 220, 222, 224 and 226 can be implemented using software, firmware and/or hardware. It is also possible that some of these detectors and trackers are implemented using software and/or firmware, with others implemented using hardware. Other variations are also possible. In accordance with a specific embodiments, each of these detectors or trackers 212, 214, 216, 218, 220, 222, 224 and 226 is implemented using software code that is stored in the memory 206 and is executed by the processor 204. The memory 206 is an example of a tangible computer-readable storage apparatus or memory having computer-readable software embodied thereon for programming a processor (e.g., 204) to perform a method. For example, non-volatile memory can be used. Volatile memory such as a working memory of the processor 204 can also be used. The computer-readable storage apparatus may be non-transitory and exclude a propagating signal.

The on-body detector 212 uses signals and/or data obtained from one or more of the above described sensors to determine whether the user-wearable device 102 is being worn by a user. For example, the on-body detector 212 can use signals/and/or data obtained from the optical sensor 122, the GSR sensor 126, the temperature sensor 130 and/or the motion sensor 132 to determine whether the user-wearable device 102 is being worn by a user. Where the user-wearable device has the form factor of a wrist-watch, e.g., as shown in FIGS. 1A and 1B, the on-body detector 212 may be referred to as a wrist-off detector or a wrist-on detector. The on-body detector 212 can be used to selective operate the device 102 in a low power mode when the on-body detector 212 detects that the device 102 is not being worn by a user. Additional details of the on-body detector 212 are described in U.S. patent application Ser. No. 14/341,248, titled "User-Wearable Devices with Power Conserving Features," which was filed Jul. 24, 2014.

The sleep detector 214 uses signals and/or data obtained from one or more of the above described sensors to determine whether a user, who is wearing the user-wearable device 102, is sleeping. For example, signals and/or data obtained using the motion sensor 132 can be used to determine when a user is sleeping. This is because people typically move around less when sleeping compared to when awake. Additionally, if the user's arm posture can be detected from the motion sensor 132, then information about arm posture can also be used to detect whether or not a user is sleeping. The sleep detector 214 can also be used to detect when a user, who is wearing the user-wearable device 102, wakes up, as well as when the user is awake.

The sleep metric detector 216 uses signals and/or data obtained from one or more of the above described sensors and/or other detectors and trackers to quantify metrics of sleep, such as total sleep time, sleep efficiency, number of awakenings, and estimates of the length or percentage of time within different sleep states, including, for example, rapid eye movement (REM) and non-REM states. The sleep metric detector 216 can, for example, use signals and/or data obtained from the motion sensor 132 and/or from the HR detector 218 to distinguish between the onset of sleep, non-REM sleep, REM sleep and the user waking from sleep. One or more quality metric of the user's sleep can then be determined based on an amount of time a user spent in the different phases of sleep. Such quality metrics can be displayed on the digital display 108 and/or uploaded to a base station (e.g., 252) for further analysis.

The HR detector 218 can use signals and/or data obtained from the PPG sensor 122 to detect HR. For example, the optical sensor 222 can be used to obtain a PPG signal from which peak-to-peak intervals can be detected, which can also be referred to as beat-to-beat intervals. The beat-to-beat intervals, which are intervals between heart beats, can be converted to HR using the equation HR=(1/beat-to-beat interval)*60. Thus, if the beat-to-beat interval=1 sec, then HR=60 beats per minute (bpm); or if the beat-to-beat interval=0.6 sec, then HR=100 bpm. The user's HR can be displayed on the digital display 108 and/or uploaded to a base station (e.g., 252) for further analysis.

The HRV detector 220 can use signals and/or data obtained from the optical sensor 122 to detect HRV. For example, in the same manner as was explained above, beat-to-beat intervals can be determined from a PPG signal obtained using the PPG sensor 122. HRV can be determined by calculating a measure of variance, such as, but not limited to, the standard deviation (SD), the root mean square of successive differences (RMSSD), or the standard deviation of successive differences (SDSD) of a plurality of consecutive beat-to-beat intervals. Alternatively, or additionally, an obtained PPG signal can be converted from the time domain to the frequency domain, and HRV can be determined using well known frequency domain techniques. The user's HRV can be displayed on the digital display 108 and/or uploaded to a base station (e.g., 252) for further analysis.

The activity detector 222 can determine a type and amount of activity of a user based on information such as, but not limited to, motion data obtained using the motion sensor 132, heart rate as determined by the HR detector 218, skin temperature as determined by the skin temperature sensor 130, and time of day. The activity detector 222 can using motion data, obtained using the motion sensor 132, to determine the number of steps that a user has taken with a specified amount of time (e.g., 24 hours), as well as to determine the distance that a user has walked and/or run within a specified amount of time. Activity metrics can be displayed on the digital display 108 and/or uploaded to a base station (e.g., 252) for further analysis.

The calorie burn detector 224 can determine a current calorie burn rate and an amount of calories burned over a specified amount of time based on motion data obtained using the motion sensor 132, HR as determined using the HR detector 218, and/or skin temperature as determined using the skin temperature sensor 130. A calorie burn rate and/or an amount of calories burned can be displayed on the digital display 108 and/or uploaded to a base station (e.g., 252) for further analysis.

The time and date tracker 226 can keep track of the time of day, date, and/or the like, which are typically tracked by a digital wristwatch. The time and date can be displayed on the digital display 108. Additionally, the time and date tracker 226 of the user-wearable device can be synced with a similar tracker of the base station 252. The time and data tracker 226 can provide time of day and date information to the other detectors described herein.

The user-wearable device 102 can include less modules than shown in FIG. 2, more modules than show and/or alternative types of modules. For example, the user-wearable device 102 can also include a body water content module and/or a body fat content module that calculates the user's body water content and/or body fat percentage based on measurements obtained using the BIA sensor 120. For another example, the user-wearable device 102 can include a stress module that estimates a user's stress level based on measures obtained using the GSR sensor 126, the ECG sensor 128 and/or the skin temperature sensor 130. These are just a few examples of other types of modules or detectors that can be included within user-wearable device 102, which are not intended to be all encompassing.

In accordance with certain embodiments, the optical sensor 122 is implemented as an integrated sensor module, examples of which are described below with reference to FIGS. 4A-6B. In each such embodiment, the optical sensor 122 includes one or more light sources and one or more light detectors. More specifically, in in accordance with specific embodiments, the integrated sensor module includes at least one packaged light source semiconductor device (PLSSD) and at least one packaged light detector semiconductor device (PLDSD), which are attached to a substrate and covered by a pre-molded cover structure. In other words, in specific embodiments, each light source is implemented as a PLSSD, and each light detector is implement as a PLDSD, examples of which are described below with reference to FIGS. 3A and 3B.

Figure 3A:
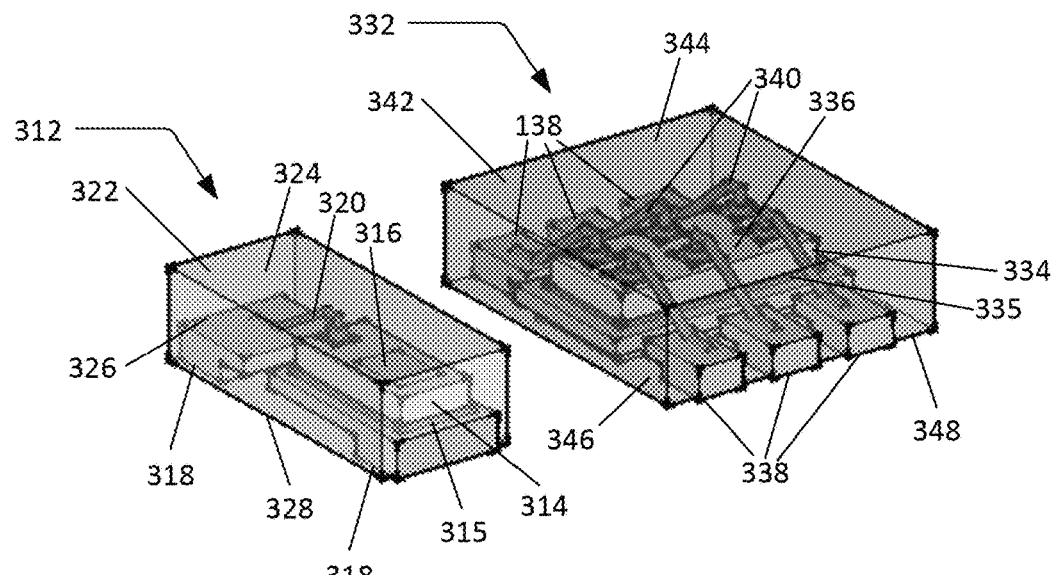
FIG. 3A shows a perspective view of an exemplary packaged light source semiconductor device (PLSSD), and a perspective view of an exemplary packaged light detector semiconductor device (PLDSD), which may be parts of the optical sensor included in the user-wearable device of FIGS. 1A, 1B and 2.
Figure 3B:
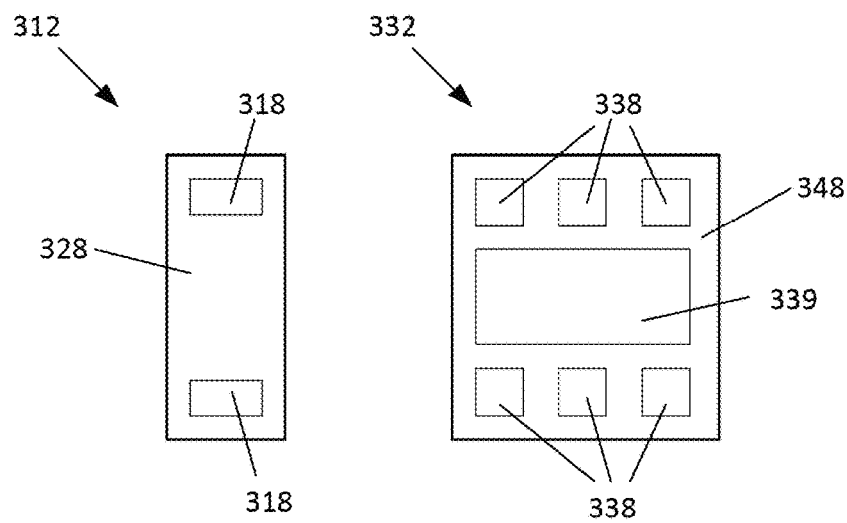
FIG. 3B shows a bottom view of the exemplary PLSSD shown in FIG. 3A, and a bottom view of the exemplary PLDSD shown in FIG. 3A.

FIG. 3A shows a perspective view of an exemplary packaged light source semiconductor device (PLSSD) 312, and a perspective view of an exemplary packaged light detector semiconductor device (PLDSD) 332. FIG. 3B shows a bottom view of the exemplary PLSSD 312 shown in FIG. 3A, and a bottom view of the exemplary PLDSD 332 shown in FIG. 3A. Both the PLSSD 312 and the PLDSD 332 can more generically be referred to as packaged optoelectronic semiconductor devices (POSDs).

The PLSSD 312 is shown as including a light source die 314 encapsulated within a light transmissive molding compound 322. The light source die 314 is shown as including one light emitting element 316, but can include more than one light emitting element 316. The light emitting element 316 can be a light emitting diode (LED), an organic LED (OLED), a bulk-emitting LED, a surface-emitting LED, a vertical-cavity surface-emitting laser (VCSEL), a superluminescent light emitting diode (SLED), a laser diode, or a pixel diode, but is not limited thereto. Light emitting elements, such as those mentioned above, are examples of optoelectronic elements.

The light transmissive molding compound 322 can be, e.g., a light transmissive epoxy (e.g., a clear or tinted epoxy), or other light transmissive resin or polymer. In certain embodiments, the light transmissive molding compound may have a pigment or other property that filters out light of certain wavelengths that are not of interest, while allowing light of wavelengths of interest to pass.

The light source die 314 is connected to electrical contacts 318 (which can alternatively be referred to as electrical connectors) by one or more die pads 315 below the die 314 and/or one or more bond wires 320. For example, one of the electrical contacts 318 can provide the contact for the anode(s) of the light emitting element(s) 316, while another one of the electrical contacts 318 can provide the contact for the cathode(s) of the light emitting element(s) 316. The light source die 314 can also include amplifier circuitry and/or other types of signal processing circuitry.

The PLSSD 312 includes a top surface 324, a bottom surface 328 and a peripheral surface 326 extending between the top surface 324 and the bottom surface 328. In this example, the top surface 324 of the PLSSD 312 is formed by a top surface of the light transmissive molding compound 322 (that encapsulates the light emitting element 316), and the peripheral surface 326 is formed by the four sides of the light transmissive molding compound 322. The bottom surface 328 includes the electrical contacts 318 for the light emitting element(s) 316, as best seen in FIG. 3B. The electrical contacts 318 can be, e.g., electrically conductive lands, electrically conductive pads, or electrically conductive balls, but are not limited thereto. For example, it is also possible that the electrical contacts 318 can be electrically conductive pins or wires. In this example, the PLSSD 312 includes two electrical contacts 318 on the bottom surface 328. In accordance with an embodiment, the PLSSD 312 is a flat no-leads package. In accordance with a specific embodiment, the electrical contacts 318 form a land grid array.

The PLDSD 332 is shown as including a light detector die 334 encapsulated within a light transmissive molding compound 342. The light detector die 334 is shown as including one light detecting element 336, but can include more than one light detecting element 336. The light detecting element 336 can be a photoresistor, a photovoltaic cell, a photodiode, a phototransistor, or a charge-coupled device (CCD), but is not limited thereto, and preferably can be used to produce a current or voltage indicative of the magnitude and/or phase of detected light. Light detecting elements, such as those mentioned above, are also examples of optoelectronic elements.

The light transmissive molding compound 342 can be, e.g., a light transmissive epoxy (e.g., a clear or tinted epoxy), or other light transmissive resin or polymer. In certain embodiments, the light transmissive molding compound may have a pigment or other property that filters out light of certain wavelengths that are not of interest, while allowing light of wavelengths of interest to pass. The light transmissive molding compound 342 of the PLDSD 332 can be the same as, or different than, the light transmissive molding compound 322 of the PLSSD 312.

The light detector die 334 is electrically connected to electrical contacts 338 (which can alternatively be referred to as electrical connectors) by one or more die pads 335 below the die 334 and/or one or more bond wires 340. For example, one or more of the electrical contacts 338 can provide the contact for the anode(s) of the light detecting element(s) 336, while one or more other electrical contacts 338 can provide the contact for the cathode(s) of the light detecting element(s) 336. The light detector die 334 can also include amplifier circuitry, filter circuitry and/or other types of signal processing circuitry.

The PLDSD 332 includes a top surface 344, a bottom surface 348 and a peripheral surface 346 extending between the top surface 344 and the bottom surface 348. In this example, the top surface 344 of the PLDSD 332 is formed by a top surface of the light transmissive molding compound 342 (that encapsulates the light detecting element 336), and the peripheral surface 346 is formed by the four sides of the light transmissive molding compound 342. The bottom surface includes the electrical contacts 338 for the light detecting element(s) 336, as best seen in FIG. 3B. The electrical contacts 338 can be, e.g., electrically conductive lands, electrically conductive pads, or electrically conductive balls, but are not limited thereto. For example, it is also possible that the electrical contacts 338 can be electrically conductive pins or wires. In this example, the PLSSD 312 includes six electrical contacts 338 and an exposed thermal pad 339 on the bottom surface 348. The exposed pad 339 can alternatively, or additionally, be a ground plane for the PLDSD 332. In accordance with an embodiment, the PLDSD 332 is a flat no-leads package. In accordance with a specific embodiment, the electrical contacts 338 form a land grid array.

Figure 4C:
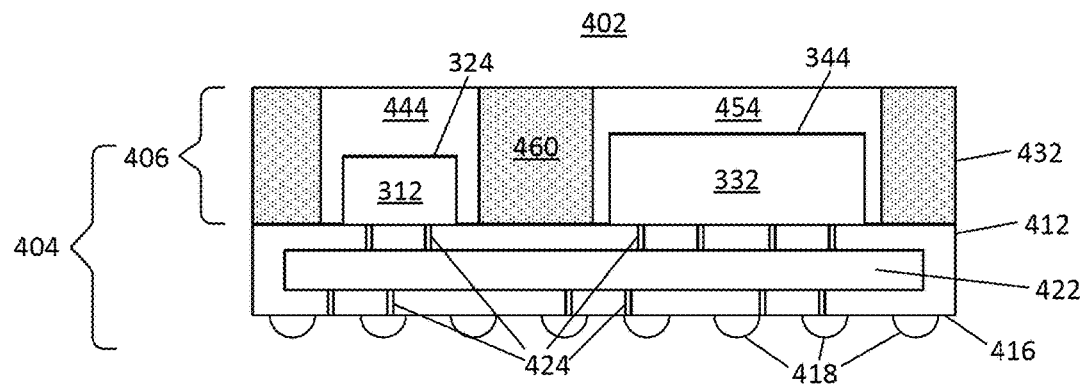
FIG. 4C is a cross section of the two subassemblies shown in FIGS. 4A and 4B after they have been attached to one another.
Figure 4D:
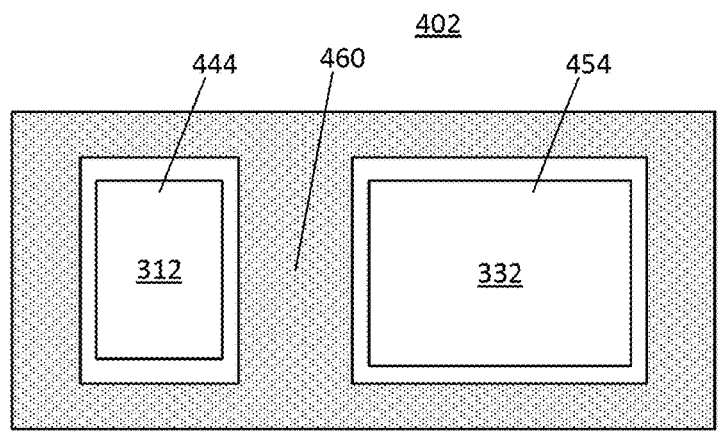
FIG. 4D is a top view of the integrated sensor module after the two subassemblies shown in FIGS. 4A and 4B have been attached to one another.

FIG. 4A is top perspective view of two subassemblies 404, 406 of an integrated sensor module 402, according to an embodiment of the present technology, before the two subassemblies 404, 406 are attached to one another. FIG. 4B is a cross section of the two subassemblies 404, 406 shown in FIG. 4A. FIG. 4C is a cross section of the two subassemblies 404, 406 shown in FIGS. 4A and 4B after they have been attached to one another. FIG. 4D is a top view of the integrated sensor module 402 after the two subassemblies 404, 406 introduced in FIGS. 4A and 4B have been attached to one another.

Referring to FIGS. 4A and 4B, the subassembly 404 includes a substrate 412 having a top surface 414 and a bottom surface 416. In accordance with an embodiment, the substrate 412 is a printed circuit board (PCB). Alternatively, the substrate 412 can be a ceramic substrate. Other substrate materials are also possible, and within the scope of the embodiments described herein. The PLSSD 312 and the PLDSD 332 are mounted to the top surface 414 of the substrate 412 such that there is a gap between the PLSSD 312 and the PLDSD 332. As shown in FIG. 4B, the bottom surface 416 of the substrate 412 is shown as including a plurality of electrically conductive balls 418 that collectively form a ball grid array (BGA). Alternatively, the bottom surface 416 of the substrate 412 can include alternative types of electrical contacts in place of the electrically conductive balls 418, such as, but not limited to, electrically conductive lands, electrically conductive pads, electrically conductive pins or wires.

The subassembly 406 includes a pre-molded cover structure 432 including a portion of which is molded from an opaque molding compound and a further portion of which is molded from a light transmissive molding compound. In other words, the cover structure 432 is co-molded from both an opaque molding compound and a light transmissive molding compound. In FIGS. 4B-4D, the portions of the pre-molded cover structure 432 that are molded from an opaque molding compound are shown as being shaded, and the portions that are molded from a light transmissive molding compound are not shaded.

The pre-molded cover structure 432 includes a pre-molded cavity 442 covered by a window 444 formed of the light transmissive molding compound. Additionally, the pre-molded cover structure 432 includes further pre-molded cavity 452 covered by a further window 454 formed of the light transmissive molding compound. In an embodiment, the pre-molded cavity 442 has dimensions that are equal to dimensions of the PLSSD 312 plus a tolerance (in each of length, width and height) so that the PLSSD 312 completely fits within the pre-molded cavity 442. Similarly, the pre-molded cavity 452 has dimensions that are equal to dimensions as the PLDSD 332 plus a tolerance (in each of length, width and height) so that the PLDSD 332 completely fits within the pre-molded cavity 452. The "tolerance" is a matter of some engineering judgment but is enough to allow the pre-molded cover structure 432 to be readily placed over the PLSSD 312 and the PLSSD 312. For example, a tolerance of about 1 mm in each of the each of length, width and height is believed appropriate. Larger or smaller tolerances are also possible.

The pre-molded cover structure 432 also includes a barrier 460 formed of the opaque molding compound between the pre-molded cavity 442 and the pre-molded cavity 452. The opaque molding compound can be, e.g., a black or other dark epoxy, or other resin or polymer that is non-transmissive to the light generated by the PLSSD 312.

The light transmissive molding compound that is used to form the windows 444 and 454 can be a light transmissive epoxy (e.g., a clear or tinted epoxy) or another light transmissive resin or polymer, but is not limited thereto. In accordance with an embodiment, in order to reduce and preferably minimize specular reflections the light transmissive molding compound that is used to form the window 444 has an index of refraction that is substantially the same as an index of refraction of the light transmissive molding compound that encapsulates the one or more light emitting elements of the light emitter die 314 of the PLSSD 312. Additionally, the light transmissive molding compound that is used to form the window 454 has an index of refraction that is substantially the same as an index of refraction of the light transmissive molding compound that encapsulates the one or more light detecting elements of the light detector die 334 of the PLDSD 332. In an embodiment, the same type of light transmission molding compound, having the same index of refraction, is used to encapsulate the light emitting element(s) of the light emitter die 314 of the PLSSD 312, to encapsulate the light detecting element(s) of the light detector die 334 of the PLDSD 332, and to form the windows 444 and 454 of the pre-molded cover structure 432.

As shown in FIG. 4C, the pre-molded cover structure 432 is attached to the substrate 412 such that the PLSSD 312 is positioned within the pre-molded cavity 442, the PLDSD 332 is positioned within the pre-molded cavity 452, the barrier 460 is positioned between the PLSSD 312 and the PLDSD 332, the window covers 444 the one or more light emitting elements of the light emitter die 314 of the PLSSD 312, and the window 454 covers the one or more light detecting elements of the light detector die 334 of the PLDSD 332. The barrier 460, which is formed of the opaque molding compound (and thus, can also be referred to as the opaque barrier 460) optically isolates the PLSSD 312 and the PLDSD 332 from one another. The opaque molding compound also forms a barrier around the periphery of the integrated sensor module 402, so as to optically isolate the module 402 from one or more other optoelectronic modules or apparatus(es) that may be located in the vicinity of the module 402.

In accordance with an embodiment, a light transmissive adhesive is dispensed between the top surface 324 of the PLSSD 312 and a bottom surface of the window 444. The light transmissive adhesive helps to attach the subassemblies 404, 406 to one another. Additionally, the light transmissive adhesive fills in any air gap that may otherwise exist between the top surface 324 of the PLSSD 312 and the bottom surface of the window 444. In order to reduce and preferably minimize reflections at the interface between the PLSSD 312 and the 444 window, an index of refraction of the light transmissive adhesive is substantially the same as the index of refraction of the light transmissive molding compound that encapsulates the light emitting element(s) of the light emitter die 314 of the PLSSD 312, and is substantially the same as an index of refraction of the light transmissive molding compound of which the window 444 is formed. Similarly, a light transmissive adhesive is dispensed between the top surface 344 of the PLDSD 332 and a bottom surface of the window 454 to help attach the subassemblies 404, 406 to one another and to fill in any air gap that may otherwise exist between the top surface 344 of the PLDSD 332 and the bottom surface of the window 454. In order to reduce and preferably minimize reflections at the interface between the PLDSD 332 and the window 454, an index of refraction of the light transmissive adhesive is substantially the same as the index of refraction of the light transmissive molding compound that encapsulates the light detecting element(s) of the light detector die 334 of the PLDSD 332, and is substantially the same as an index of refraction of the light transmissive molding compound of which the window 454 is formed. In accordance with an embodiment, the same type of light transmissive adhesive is dispensed between the top surface 324 of the PLSSD 312 and the bottom surface of the window 444 as is dispensed between the top surface 344 of the PLDSD 332 and the bottom surface of the window 454. Additionally, to attach the subassemblies 404, 406, an adhesive, which can be an opaque adhesive, attaches a bottom surface 462 of the pre-molded cover structure 432 to the top surface 414 of the substrate 412.

In accordance with an embodiment, a die 422 is embedded within the substrate 402 between the top and bottom surfaces 404, 406 of the substrate 402. The embedded die 422 can, e.g., include analog and/or digital circuitry used to drive the one or more light emitting elements of the light emitter die 314 of the PLSSD 312. Additionally, or alternatively, the die 422 can include analog and/or digital circuitry to perform signal processing on a signal produced by the one or more light detecting elements of the light detector die 334 of the PLDSD 332. For a more specific example, the analog circuitry can be an analog front end that performs transimpedance amplification, analog signal filtering, and/or analog signal amplification of a signal produced by the one or more light detecting elements of the light detector die 334 of the PLDSD 332. The die 422 can also include an analog-to-digital converter, digital signal processing circuitry and/or communication interfaces. It is also possible that more than one die is embedded within the substrate 412. It is also possible that circuitry associate with one or more of the sensors described herein be included within a die that is embedded within the substrate 412. In addition to (or instead of) the die 422 being embedded within the substrate 412, one or more discrete circuit components can be embedded with the substrate 412. Metal vias 424 within the substrate 402 are used to electrically connect the PLSSD 312 and the PLDSD 332 to the embedded die 422 (and/or discrete circuit components), and to electrically connect the embedded die 422 (and/or discrete circuit components) to the electrically conductive balls 418 or other types of electrical contacts that are on the bottom surface of the substrate 412. Metal vias 424 may also electrically connect the PLSSD 312 and the PLDSD 332 directly to the electrically conductive balls 418 or other types of electrical contacts that are on the bottom surface of the substrate 412. Additionally, there can be electrically conductive traces on the upper surface 414 of the substrate 412, the bottom surface 416 of the substrate 412 and/or within the substrate 412 that provide (alone or in combination with the metal vias 424) for electrical connections between the various electrical components described herein.

Figure 5:
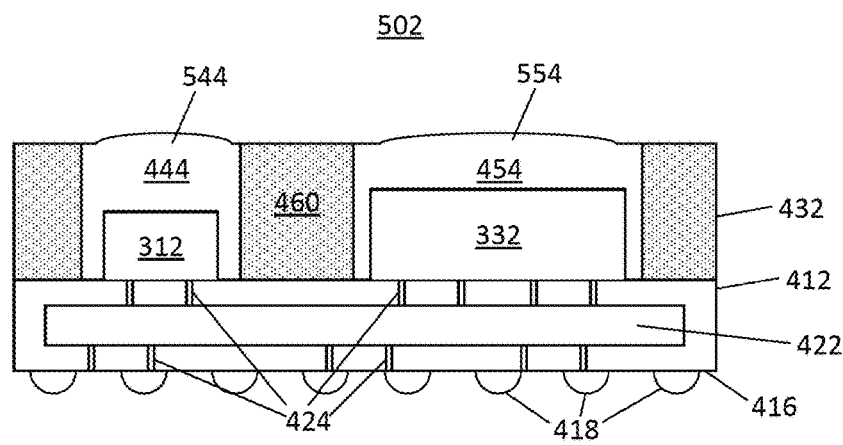
FIG. 5 is a cross section of an integrated sensor module that is similar to the one shown in FIGS. 4A-4D, but includes windows having lenses.

FIG. 5 is a cross section of an integrated sensor module 502 that is similar to the module 402 shown in FIGS. 4A-4D, but includes windows having lenses. More specifically, the window 444 is shown as including an integrally formed convex lens 544 which can be used to focus the light emitted by the light emitting element(s) of the light emitter die 314 of the PLSSD 312. Further, the window 454 is shown as including an integrally formed convex lens 554 which can be used to focus light that is incident on the module 502 towards the light detecting element(s) of the light detector die 334 the PLDSD 332. It is also possible that the lenses 544, 554 are separately formed and then attached to the windows 444 and 454. It is also possible that only one of the windows includes a lens, while the other does not. Other shapes for the lens(es) is/are also possible.

Figure 6A:
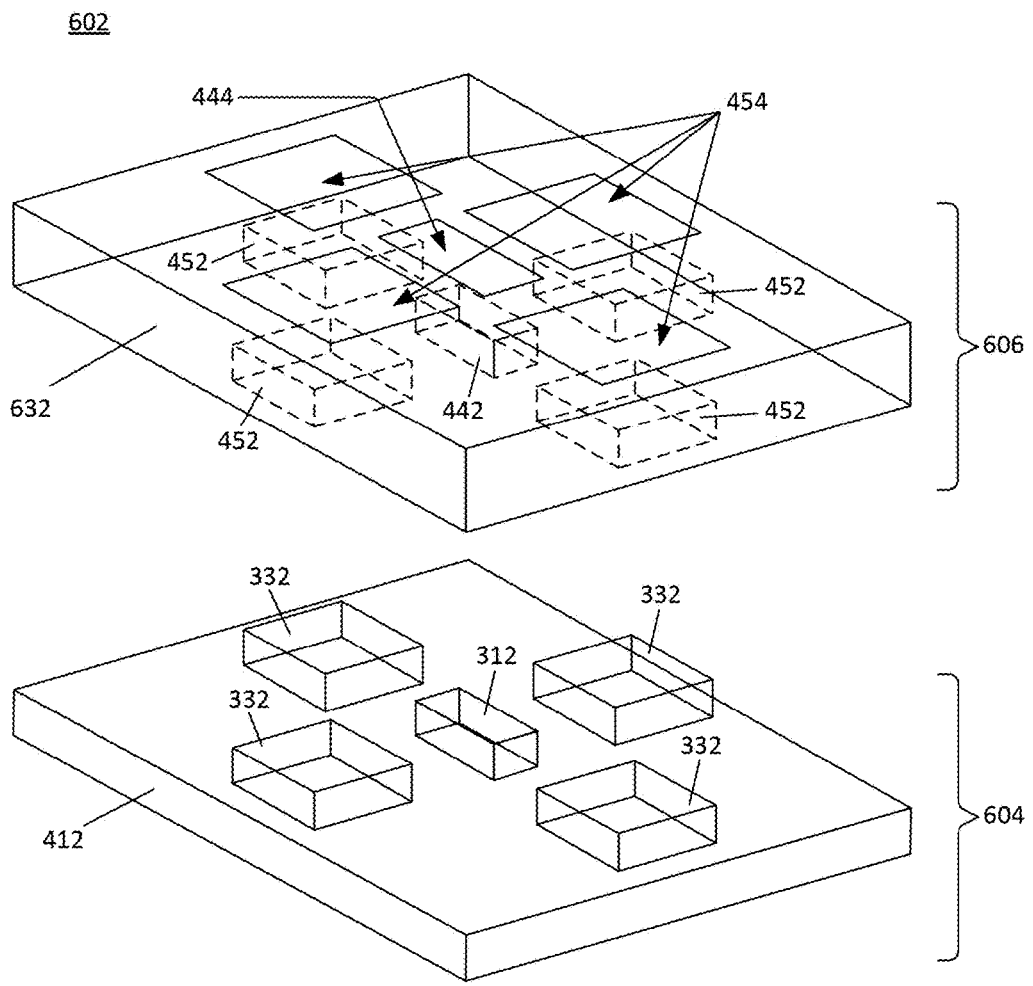
FIG. 6A is top perspective view of two subassemblies of an integrated sensor module, according to another embodiment of the present technology, before the two subassemblies are attached to one another.
Figure 6B:
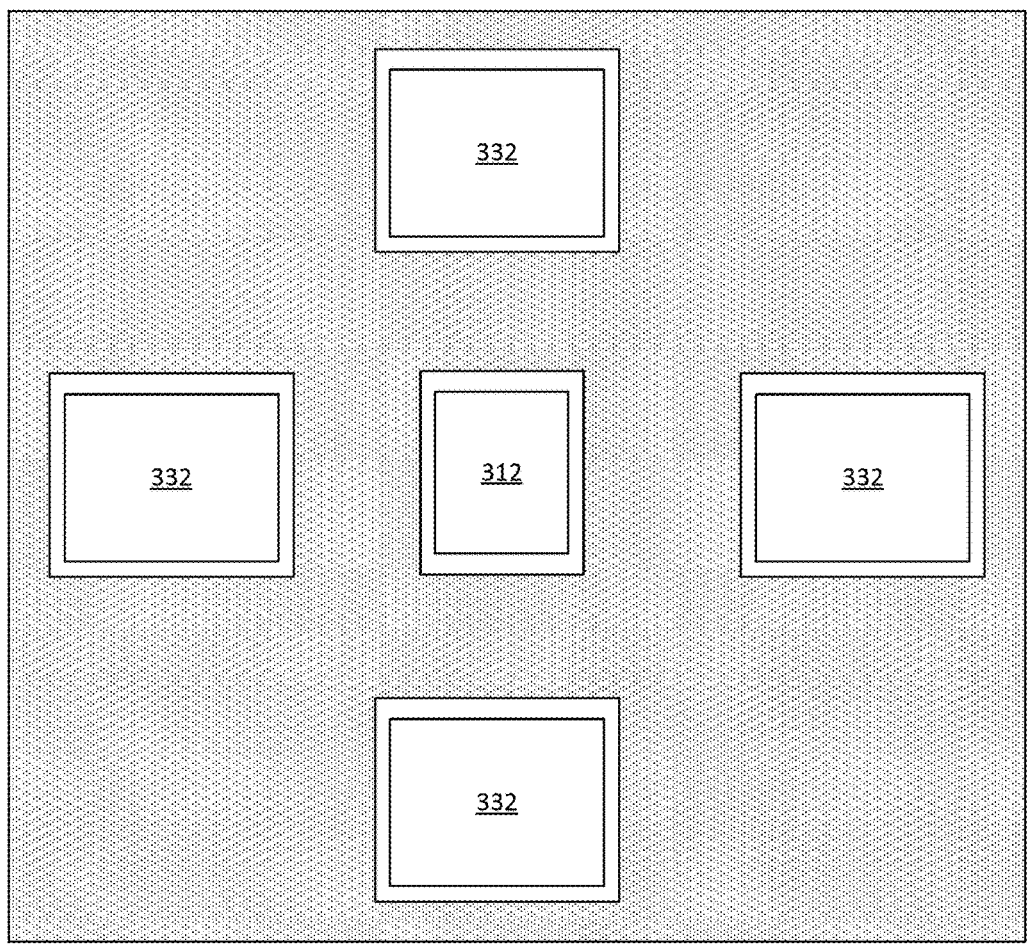
FIG. 6B is a top view of the integrated sensor module introduced in FIG. 6A after the two subassemblies shown in FIG. 6A have been attached to one another.

In the embodiments described with reference to FIGS. 4A-4D and 5, the sensor modules 402, 502 were described and shown as including one PLSSD 312 and one PLDSD 332. Other variations are possible, and within the scope of embodiments of the present technology, wherein in such other variations one or more PLSSD(s) 312 is/are mounted to a top surface of a substrate, and one or more PLDSD(s) 332 is/are also mounted to the top surface of the substrate, and a pre-molded cover structure including a cavity and window for each of the PLSSD(s) 312 and PLDSD(s) 332. In such embodiments, an opaque barrier of the pre-molded cover structure preferably optically isolates each of the PLSSD(s) 312 and the PLDSD(s) 332 from one another. FIGS. 6A and 6B, described below, provides one example of such an alternative embodiment. However, one of ordinary skill in the art reading this disclosure would understand that other variations are also within the scope of embodiments of the present technology.

FIG. 6A is top perspective view of two subassemblies 604, 606 of an integrated sensor module 602, according to an embodiment of the present technology, before the two subassemblies 604, 606 are attached to one another. FIG. 6B is a top view of the integrated sensor module 602 after the two subassemblies shown in FIG. 6A have been attached to one another. In the embodiment shown in FIGS. 6A and 6B, there is one PLSSD 312 are four PLDSDs 332 that are mounted to the top surface of the substrate 412 such that the PLSSD 312 is positioned in a middle between the four PLDSDs 332, and such that there is a respective gap between the PLSSD 312 and each of the four PLDSDs 332. Here, a pre-molded cover structure 632 includes one cavity 442 for the PLSSD 312, and four cavities 452 for the PLDSDs 332. The cavity 442 is covered by a window 444, and each of the cavities 454 is covered by a respective window 454. Exemplary dimensions of the integrated sensor module 602 are 6 mm×6 mm×1.6 mm, but are not limited thereto. The subassemblies 602, 604 can be attached to one another in a similar manner as the subassemblies 402, 404 were described above as being attached to one another.

The integrated sensor module 602 can be used to implement certain embodiments described in U.S. patent application Ser. No. 14/341,803, entitled "Sensor System for Heart Rate Measurement Per Axis of Shared Orientation," filed Jul. 26, 2014. For example, the integrated sensor module 602, or a similar integrated sensor module according to an embodiment described herein, can be used in a method for active motion artifact compensation of heart rate data based on measurements taken for at least one axis of orientation shared by light processing elements of a PPG optical sensor and an accelerometer.

An integrated sensor module (e.g., 402, 502 or 602, but not limited thereto) of an embodiment of the present technology can be included in a user-wearable device, such as the wrist worn device described with reference to FIGS. 1A, 1B, 1C and 2. More specifically, an integrated sensor module (e.g., 402, 502 or 602, but not limited thereto) of an embodiment described herein can be used as the optical sensor 122 shown in and described with reference to FIGS. 1B and 2. In accordance with an embodiment, a caseback of the housing 104 includes one or more openings that are intended to be aligned with the windows (e.g., 444, 454) of one of the integrated sensor modules described herein. Alternatively, an integrated sensor module can be used as the caseback. Embodiments of the present technology are also directed to user-wearable devices that include an integrated sensor module described herein. An integrated sensor module (e.g., 402, 502 or 602, but not limited thereto) of an embodiment of the present technology can alternatively be included in other types of devices, such as, but not limited to, a mobile phone, a tablet computer, or a laptop computer.

Figure 7:
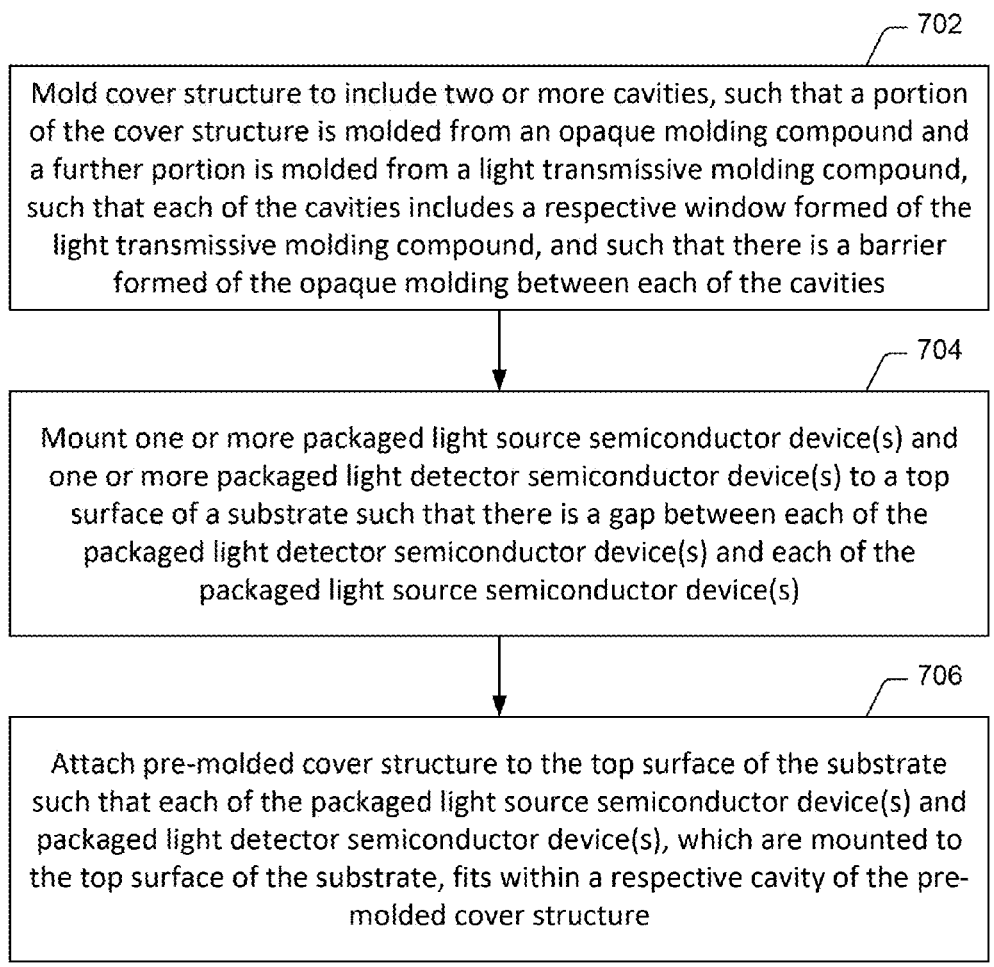
FIG. 7 is a high level flow diagram of a method for manufacturing integrated sensor module according to an embodiment of the present technology.

FIG. 7 is a high level flow diagram of a method for manufacturing an integrated sensor module according to an embodiment of the present technology. Referring to FIG. 7, at step 702, a cover structure (often referred to herein as a pre-molded cover structure) including two more cavities is molded such that a portion thereof is molded from an opaque molding compound and a further portion thereof is molded from a light transmissive molding compound, such that each of the cavities is covered by a respective window formed of the light transmissive molding compound, and such that there is a barrier formed of the opaque molding between each of the cavities. Molding techniques that can be used include, but are not limited to, injection molding, compression molding, transfer molding and cast molding, or combinations thereof. Step 702 can be performed well before (i.e., at a much earlier time than) the remaining steps described below, and may be performed in a different facility than the remaining steps described below. Cavities for one or more additional sensors, such as a packaged temperature sensor semiconductor device, can also be molded or otherwise formed in the cover structure. Additionally, as will be described in additional detail below, with reference to FIGS. 8A and 8B, a thermally conductive metal structure (e.g., 830 in FIG. 8A) can be included in the molded cover structure. Cavities for one or more electrodes can also be molded or otherwise formed in the cover structure. Additionally, as will be described in additional detail below, with reference to FIGS. 8A and 8B, one or more electrically conductive metal structures (e.g., 866a and 866b in FIG. 8A) can be included in the molded cover structure. In certain embodiments, described below with reference to FIGS. 9A and 9B, the cover structure can be co-molded such that one or more electrodes (e.g., 912a and 912b in FIG. 9A) extend from a respective portion of a top surface of the pre-molded cover structure past a bottom surface of the pre-molded cover structure and thereby extend from the bottom surface of the pre-molded cover structure.

At step 704, one or more packaged light source semiconductor device(s) and one or more packaged light detector semiconductor device(s) are mounted to a top surface of a substrate such that there is a gap between each of the packaged light detector semiconductor device(s) and each of the packaged light source semiconductor device(s). Such mounting can be performed, e.g., using a solder paste. Additionally, or alternatively, a solder reflow process can be performed. Other mounting techniques are also possible. One or more additional sensors, such as a packaged temperature sensor semiconductor device, can also be mounted to the top surface of the substrate.

At step 706, the pre-molded cover structure (molded at step 702) is attached to the top surface of the substrate such that each of the packaged light source semiconductor device(s) and packaged light detector semiconductor device(s), which are mounted to the top surface of the substrate, fits within a respective cavity of the pre-molded cover structure. Step 706 can include dispensing a light transmissive adhesive within each of the cavities and/or dispensing the light transmissive adhesive on a top surface of each of the packaged light source semiconductor device(s) and packaged light detector semiconductor device(s). In specific embodiments, the light transmissive adhesive has an index of refraction that is substantially the same as an index of refraction of the light transmissive molding compound from with the windows are formed. Additionally, the index of refraction of the light transmissive adhesive can also be substantially the same of an index of refraction of a light transmissive molding compound that is used to encapsulate light emitting element(s) and light detecting element(s) of the packaged light source semiconductor device(s) and packaged light detector semiconductor device(s). Step 706 can also include dispensing an opaque adhesive on a top surface of the substrate and/or on a bottom surface of the pre-molded cover structure, to adhere such surfaces to one another.

Figure 8A:
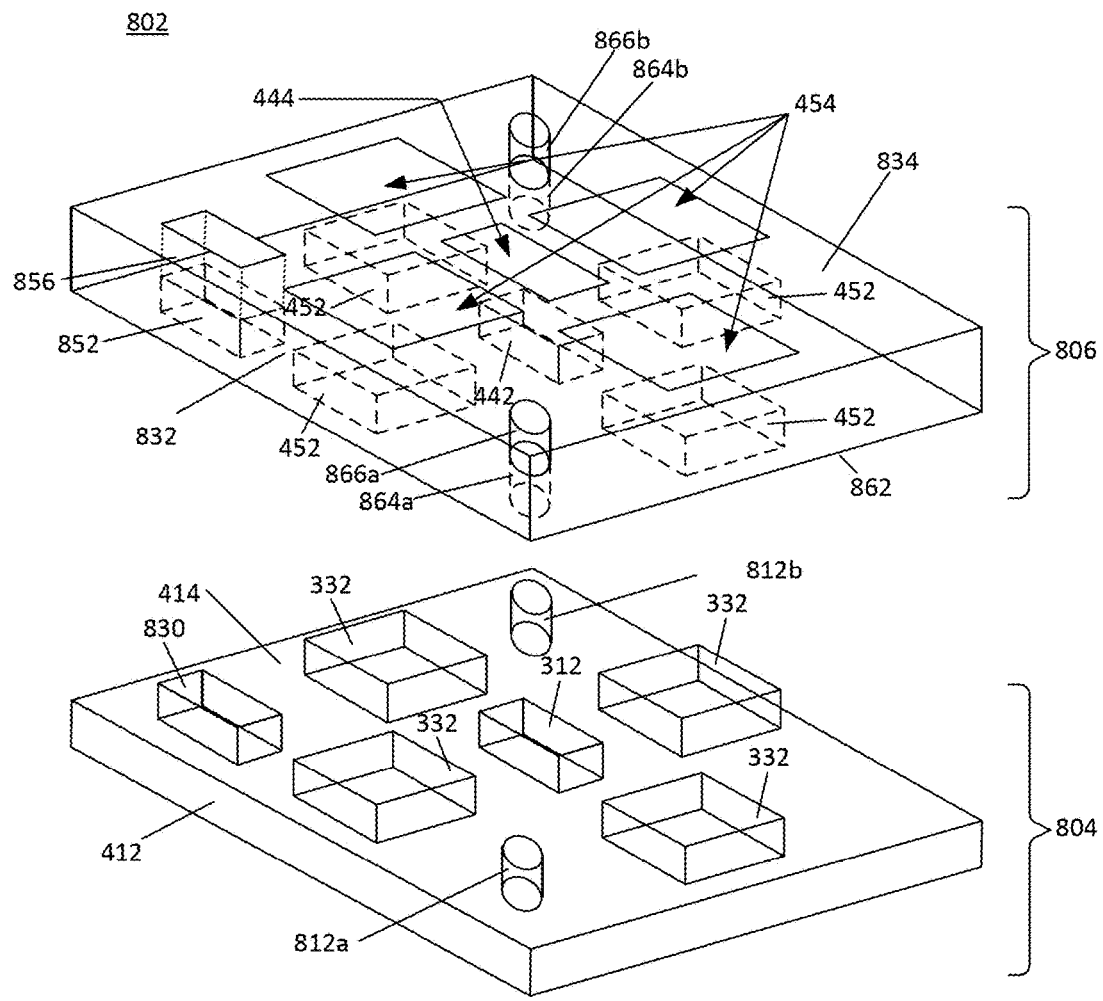
FIG. 8A is top perspective view of two subassemblies of an integrated sensor module, according to another embodiment of the present technology, before the two subassemblies are attached to one another.
Figure 8B:
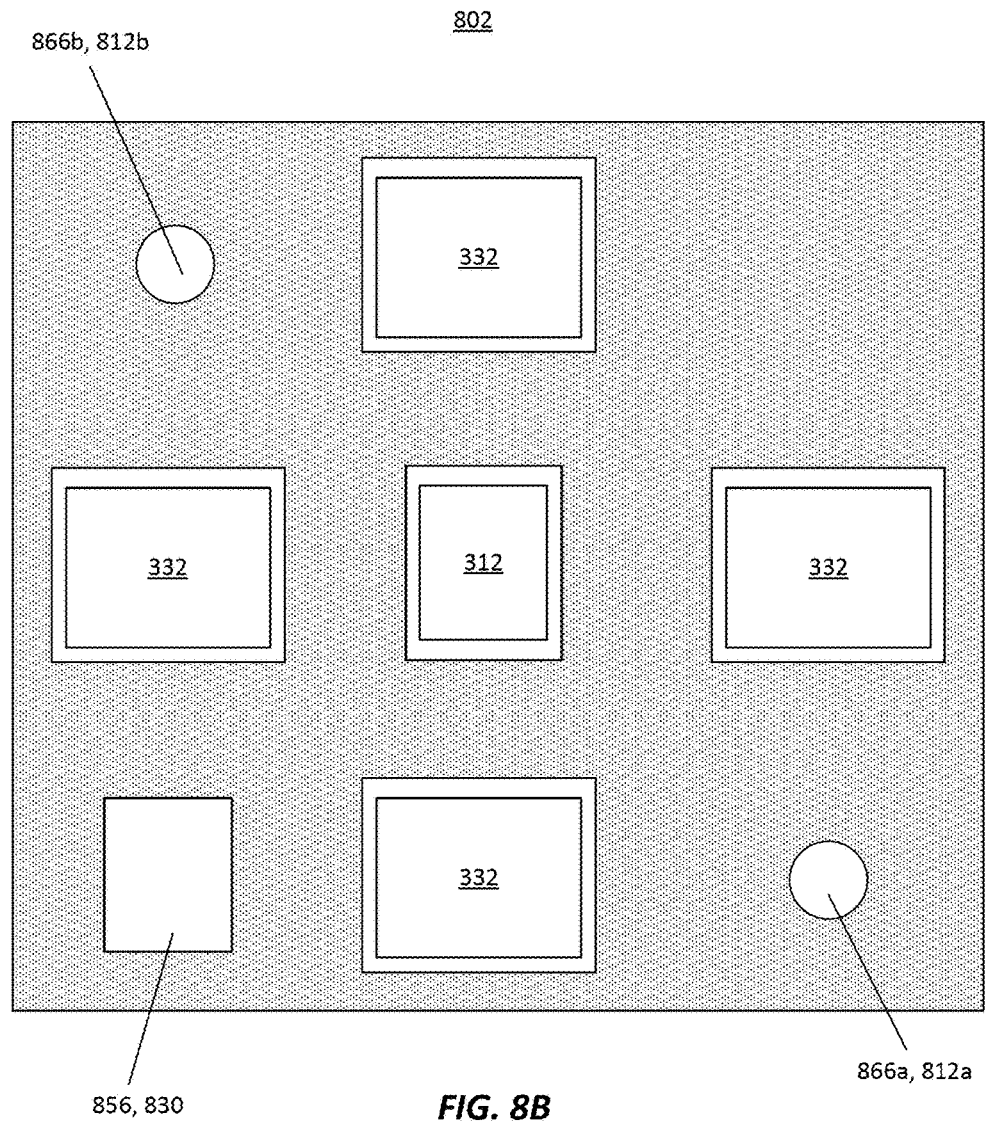
FIG. 8B is a top view of the integrated sensor module introduced in FIG. 8A after the two subassemblies shown in FIG. 8A have been attached to one another.

In accordance with certain embodiments, an integrated sensor module includes one or more sensors and/or electrodes in addition to the optical sensor 122. An example of such an integrated sensor module 802 will now be described with reference to FIGS. 8A and 8B. Referring to FIGS. 8A and 8B, the integrated sensor module 802 is shown as including one PLSSD 312 are four PLDSDs 332 that are mounted to the top surface of the substrate 412 such that the PLSSD 312 is positioned in a middle between the four PLDSDs 332, and such that there is a respective gap between the PLSSD 312 and each of the four PLDSDs 332. The PLSSD 312 and PLDSDs 332 are components of the optical sensor 122. Also mounted to the top surface 414 of the substrate 412 is a packaged temperature sensor semiconductor device (PTSSD) 830, which is an implementation or component of the skin temperature sensor 130 discussed above. Additionally, a pair of electrodes 808a and 808b extend upward from the substrate 412. The electrodes 808a and/or 808b can be connected (e.g., selectively) to sensor circuitry associated with one or more of the sensors described above, such as sensor circuitry associated with the BIA sensor 120, the capacitive sensor 124, the GSR sensor 126 and/or ECG sensor 128.

Referring to FIG. 8A, in this embodiment, a pre-molded cover structure 832 includes one pre-molded cavity 442 for the PLSSD 312, four pre-molded cavities 452 for the PLDSDs 332, a pre-molded cavity 852 for the PTSSD 830, and two pre-molded cavities 864a and 864b for the electrodes 808a and 808b. The cavity 442 is covered by a window 444, and each of the cavities 454 is covered by a respective window 454. Located between the cavity 852 (for the PTSSD 830) and a top surface 834 of the pre-molded cover structure 832 is a metal structure 856 (e.g., a block of metal) made of a thermally conductive metal, such as, but not limited to, aluminum or copper. The purpose of the metal structure 856 is to provide a thermal coupling between the PTSSD 830 and the portion of the metal structure 856 that is generally flush with the top surface 834 of the pre-molded cover structure 832 which is intended to come in contact with a user's skin. The sides of the metal structure 856 can be surrounded by and held in place by the opaque molding compound used to form other portions of the pre-molded cover structure 832. In an embodiment, the pre-molded cavity 852 has dimensions that are equal to dimensions of the PTSSD 830 plus a tolerance (in each of length, width and height) so that the PTSSD 830 completely fits within the pre-molded cavity 852. Similarly, the pre-molded cavities 866a and 866b have dimensions that are equal to dimensions as the electrodes 808a and 808b plus a tolerance (in each of length, width and height) so that the electrodes 808a and 808b completely fit within the pre-molded cavities 866a and 866b. The electrodes 808a and 808b can be the same size as one another, or different sizes than one another.

Located between the cavity 864a and the top surface 834 of the pre-molded cover structure 832 is a metal structure 866a (e.g., a cylinder of metal) made of an electrically conductive metal, such as, but not limited to, aluminum or copper. Similarly, located between the cavity 864b and a top surface 834 of the pre-molded cover structure 832 is a metal structure 866b. The purpose of the metal structures 866a and 866b is to provide electrical couplings between the electrodes 808a and 808b and the portions of the metal structures 866a and 866b that are flush with the top surface 834 of the pre-molded cover structure 832 which is intended to come in contact with a user's skin. Explained another way, the metal structures 866a and 866b essentially extend the lengths of the electrodes 808a and 808b. The sides of the metal structures 866a and 866b can be surrounded by and held in place by the opaque molding compound used to form other portions of the pre-molded cover structure 832. In an embodiment, the inner surfaces of the pre-molded cavities 866a and 866b are plated with an electrically conductive metal plating material, such as, but not limited to, copper, aluminum or gold. In such an embodiment, the pre-molded cavities 866a and 866b act as sockets for the electrodes 808a and 808b. In accordance with an embodiment, to upper exposed surfaces of the metal structures 856, 866a and 866b are plated with chromium (also known as chrome) or some other metal or alloy that is resistant to corrosion and/or oxidation.

The subassemblies 802, 804 can be attached to one another in a similar manner as the subassemblies 402, 404 were described above as being attached to one another. In a similar manner discussed above with reference to FIGS. 4A-4D, a light transmissive adhesive can be dispensed between the top surface 324 of the PLSSD 312 and a bottom surface of the window 444 to help to attach the subassemblies 804, 806 to one another and to fill in any air gap that may otherwise exist between the top surface 324 of the PLSSD 312 and the bottom surface of the window 444, wherein an index of refraction of the light transmissive adhesive is preferably substantially the same as the index of refraction of the light transmissive molding compound that encapsulates the light emitting element(s) of the light emitter die 314 of the PLSSD 312 and the light transmissive molding compound of which the window 444 is formed. In a similar manner discussed above with reference to FIGS. 4A-4D, a light transmissive adhesive can be dispensed between the top surface 344 of the PLDSD 332 and a bottom surface of the window 454 to help attach the subassemblies 804, 806 to one another and to fill in any air gap that may otherwise exist between the top surface 344 of the PLDSD 332 and the bottom surface of the window 454, wherein an index of refraction of the light transmissive adhesive is preferably substantially the same as the index of refraction of the light transmissive molding compound that encapsulates the light detecting element(s) of the light detector die 334 of the PLDSD 332 and the light transmissive molding compound of which the window 454 is formed. Additionally, an adhesive, which can be an opaque adhesive, can attached the subassemblies 804, 806, and more specifically, attach a bottom surface 862 of the pre-molded cover structure 832 to the top surface 414 of the substrate 412.

In accordance with an embodiment, an electrically conductive grease or an electrically conductive adhesive is dispensed in the cavities 864a and 864b so that the electrically conductive grease or the electrically conductive adhesive fill in any air gap that may otherwise exist between the top surfaces of the electrodes 812a and 812b and the bottom surfaces of the metal structures 866a and 866b. The electrically conductive grease or adhesive ensures electrical conduction between the electrodes 812a and 812b and the metal structures 866a and 866b. Alternatively, or additionally, electrically conductive springs can be placed within the cavities 864a and 864b. In certain embodiments, the electrodes 812a and 812b and/or the metal structures 866a and 866b are spring loaded to ensure that the electrode 812a and the metal structure 866a contact one another, and to ensure that the electrode 812b and the metal structure 866b contact one another. When the metal structures 866a and 866b are in electrical contact with the electrodes 812a and 812b, the metal structures 866a and 866b become extensions of the electrodes 812a and 812b and can be considered parts of the electrodes 812a and 812b.

In accordance with an embodiment, a thermally conductive grease (also known as a thermal grease) or a thermally conductive adhesive is dispensed in the cavity 852 so that the thermally conductive grease or adhesive fills in any air gap that may otherwise exist between the top surface of the PTSSD 830 and the bottom surface of the metal structure 856. The thermally conductive grease or adhesive ensures thermal conduction between the PTSSD 830 and the metal structure 856. When the metal structure 865 is in thermal contact with the PTSSD 830, the metal structure 856 becomes an extension of the PTSSD 830 can be considered part of the skin temperature sensor 130.

In FIGS. 8A and 8B the electrodes 812a and 812b and the metal structures 866a and 866b were shown as being cylindrical in shape, but can alternatively have other shapes. Similarly, while the PTSSD 830 and metal structure 856 were shown as have a rectangular cuboid shape, they can alternatively have other shapes.

Figure 9A:
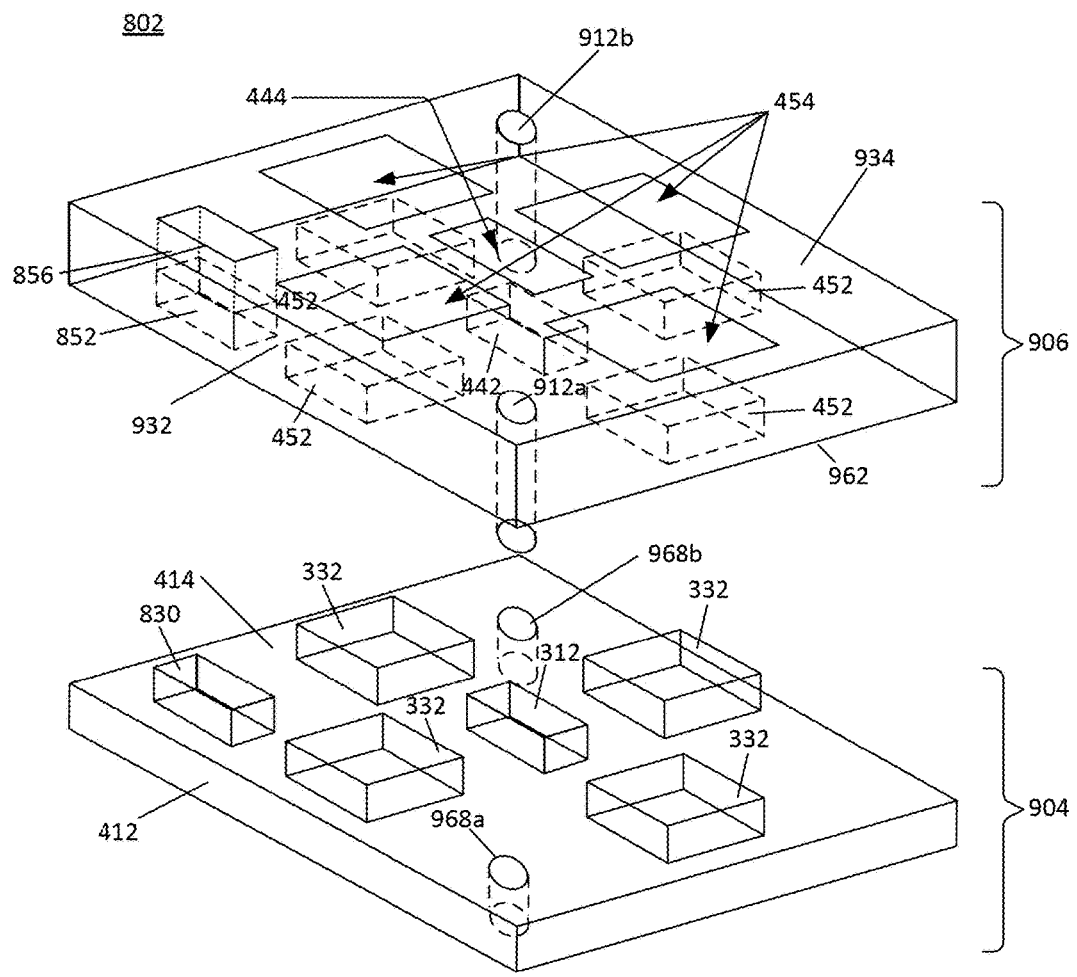
FIG. 9A is top perspective view of two subassemblies of an integrated sensor module, according to another embodiment of the present technology, before the two subassemblies are attached to one another.
Figure 9B:
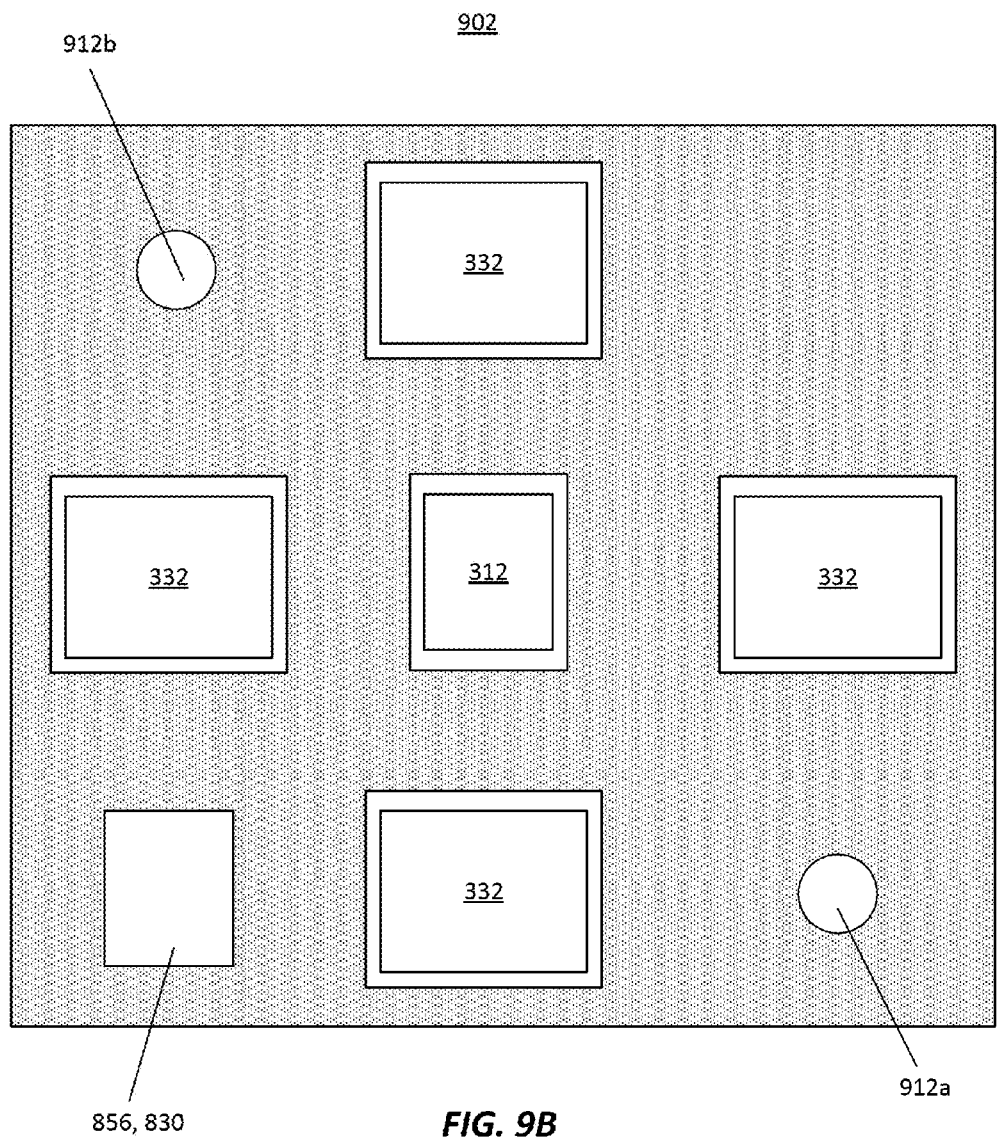
FIG. 9B is a top view of the integrated sensor module introduced in FIG. 9A after the two subassemblies shown in FIG. 9A have been attached to one another.

An integrated sensor module 902 shown in FIGS. 9A and 9B is similar to the integrated sensor module 802 described with reference to FIGS. 8A and 8B, except the integrated sensor module 902 does not include electrodes 812a and 812b extending upward from the substrate 412, and the pre-molded cover structure 832 does not include cavities/sockets 864a and 864b and metal structures 866a and 866b. Rather, a pre-molded cover structure 932 of an upper subassembly 906 includes electrodes 912a and 912b co-molded therein. The electrodes 912a and 912b are preferably made of an electrically conductive metal, such as, but not limited to, aluminum or copper. In accordance with an embodiment, upper exposed surfaces of the electrodes 912a and 912b are plated with chromium (also known as chrome) or some other metal or alloy that is resistant to corrosion and/or oxidation. The electrodes 912a and 912b extend from a top surface 934 of the pre-molded cover structure 932, all the way through the pre-molded cover structure 932, and extend downward from a bottom surface 962 of the pre-molded cover structure 932. The substrate 412 of a lower subassembly 904 includes openings or through-holes 968a and 968b that are configured to accept the lower or distal portions of the electrodes 912a and 912b that extend downward from the bottom surface 962 of the pre-molded cover structure 932. Inner surfaces of the openings or through-holes 968a and 968b can be plated with an electrically conductive metal plating material, such as, but not limited to, copper, aluminum or gold. The subassemblies 902 and 904 can be attached to one another in a similar manner as the subassemblies 402 and 404 were described above as being attached to one another. Additionally, the lower portions of the electrodes 912a and 912b, which extend downward from the bottom surface 962 of the pre-molded cover structure 932, can be soldered into the openings or through-holes 968a and 968b in the substrate 412. In this manner, soldering of the lower portions of the electrodes 912a and 912b into the openings or through-holes 968a and 968b provides for both electrical connectivity as well as mechanical connectivity between the subassemblies 904 and 906.

In the above described FIGS., the packaged light source semiconductor device(s) and the packaged light detector semiconductor device(s) (e.g., 324, 244) were shown as having rectangular cuboid shapes, and thus, the cavities (e.g., 442, 452) in the pre-molded cover structures (e.g., 432, 632) were also shown as having generally rectangular cuboid shapes. It is also within the scope of embodiments of the present technology that the packaged light detector semiconductor device(s), the packaged light detector semiconductor device(s), and the cavities in the pre-molded cover structures can have alternative shapes, such as, but not limited to, cubic, cylindrical, oval cylindrical, or half-cylindrical. In the FIGS., an outer periphery of the substrate (e.g., 412) and an outer periphery of the pre-molded cover structure (e.g., 432, 642) were shown as being rectangular. It is also within the scope of embodiments of the present technology that an outer periphery of the substrate and an outer periphery of the outer periphery of the pre-molded cover structure can have alternative shapes, such as circular, oval, pentagonal, hexagonal, octagonal, or the like. In accordance with specific embodiments, an outer periphery of the substrate (e.g., 412) and an outer periphery of the pre-molded cover structure (e.g., 432, 642) have the same shape and size so that when they are attached to one another they align with and are flush with one another. In the above described FIGS., each of the windows (e.g., 444, 454) of the pre-molded cover structure was shown as having a rectangular shape. It is also within the scope of embodiments of the present technology that the windows of the pre-molded cover structure can have alternative shapes, such as circular, oval, pentagonal, hexagonal, octagonal, or the like. In the above described FIGS. the windows of the pre-molded cover structure where shown as having a slightly larger footprint than the respective packaged light detector semiconductor device(s) and packaged light detector semiconductor device(s) that the windows cover. It is also within the scope of embodiments of the present technology that the windows can have footprints that are smaller than the footprints of the respective packaged light detector semiconductor device(s) and packaged light detector semiconductor device(s) that the windows cover. It is also within the scope of embodiments of the present technology that the relative locations of the sensors or portions thereof can be changed. Further, the relative locations of the electrodes included in the integrated sensor modules can be changed.

In the above described embodiments, where a pre-molded cavity (e.g., 442) is covered by a window (e.g., 444), the pre-molded cavity can also be said to have the window, in a similar manner that a room covered by a sky light type of window can be said to have a sky light.

Any one of the integrated sensor modules described herein can be mounted to a printed circuit board (PCB) to which is also mounted other electrical components of a device, such as a processor (e.g., 204), memory (e.g., 206) and wireless interface (208), and/or a microcontroller (e.g., 202). One or more further integrated circuitry chips and/or discrete circuitry can also be mounted to the PCB. Additionally circuitry, such as voltage regulation circuitry, and circuitry to recharge a battery (e.g., 210) can also be mounted to the PCB. Such a PCB, with the integrated sensor module mounted therein, can be included in a user-wearable device or other devices, such as mobile phones and tablet computers, but not limited thereto.

The pre-molded covers structures described herein can also include one or more cavities for additional sensors, which, depending upon the sensor that the cavity is for, may not include any window or metal structure. For example, if a motion sensor is mounted to a surface of the substrate 412, then a pre-molded cover structure can include a cavity within which the motion sensor fits. It would also be possible to include the motion sensor in a die that is embedded in the substrate, or in a device that is mounted to a PCB to which an integrated sensor module is also mounted.

In accordance with certain embodiments, one of the integrated sensor modules described herein can be shaped and otherwise designed to be utilized as the backside or caseback of the housing or case of a user-wearable device, such as the device 104 described above with reference to FIGS. 1A, 1B and 1C. Integrated sensor modules described herein can also be used in other types of user-wearable devices, as well as in other types of devices, such as mobile phones and table computers. Embodiments of the present technology are also directed to user-wearable devices, and other types of devices, that include one of the integrated sensor modules described herein.

Figure 10A:
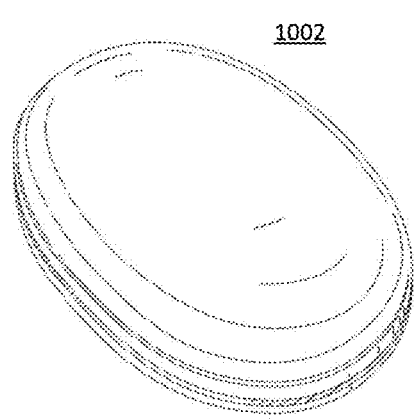
FIGS. 10A, 10B and 10C are, respectively, perspective, rear and side views of a physiological sensor pod according to an embodiment that can include an integrated sensor module.
Figure 10B:
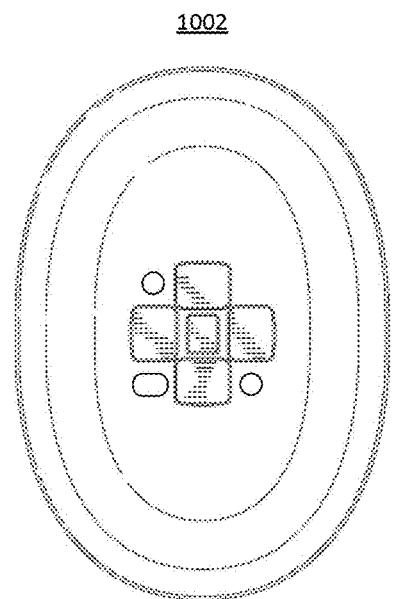
Figure 10C:
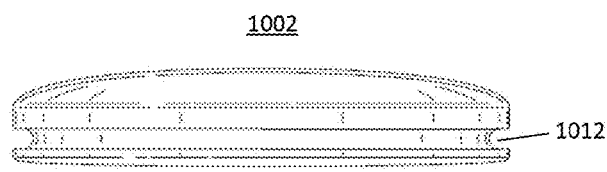
Figure 11:
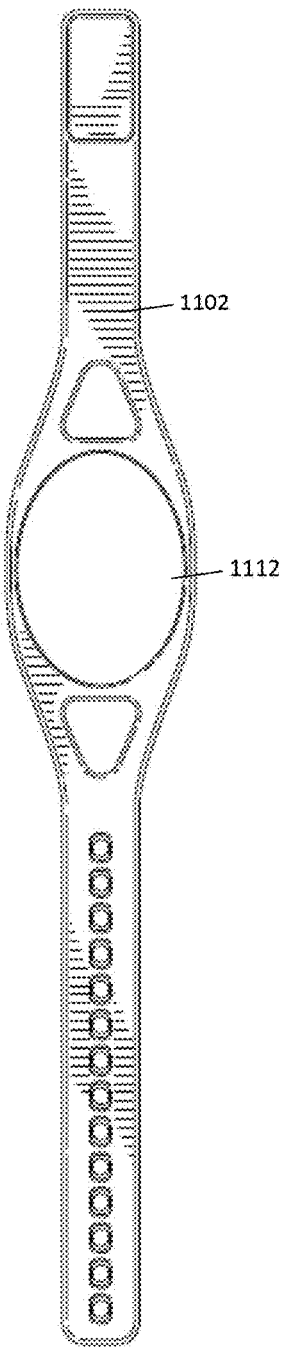
FIG. 11 illustrates a wrist band including an opening into which the physiological sensor pod introduced in FIGS. 10A, 10B and 10C can be placed.

The integrated sensor modules described herein can be included in a physiological sensor pod that can be mechanically attachable and removable from user-wearable support structure such as a wrist strap, a head band, a sock, or a shirt, but not limited thereto. An exemplary form factor of a physiologic sensor pod, which can include one of the integrated sensor modules described herein, is shown in FIGS. 10A, 10B and 10C. FIG. 10A is a front perspective view of a physiological sensor pod 1002, which can also be referred to more simply as a sensor pod. FIG. 10B is a bottom view of the sensor pod 1002. FIG. 10C is a side view of the sensor pod 1002. While not specifically shown in FIG. 10A, indicator lights and/or a display can be viewable from the top of the sensor pod 1002. As can be appreciated from FIG. 10B, one of the integrated sensor modules described herein can be used as the back of the sensor pod 1002. FIG. 10C illustrates a groove 1012 extending around a circumference of the sensor pod 1002. Referring to FIG. 11, the sensor pod 1012 can be placed within an opening 1112 in a wrist band 1102, so that the groove 1012 fits into the opening 1112 and secures the sensor pod in place. The sensor pod 1012 can alternatively be placed in a similar opening in a headband, chest strap, swim cap, arm band, or some other user wearable band or strap. In still other embodiments, the sensor pod 1012 can be placed into a pocket within a sock or tight fitting shirt (e.g., a bicycle shirt) or other article of apparel or clothing that includes a pocket for the sensor pod. Such a pocket can include an opening that enables the backside of the sensor pod, which includes windows for the optical sensor, electrodes or other sensor elements, to contact the wearer's skin to thereby enable the sensor(s) to operate properly. The opening in the pocket can also enable the groove 1012 in the sensor pod 1002 to be snapped into a correct position and held in place against a user's skin. The sensor pod 1012 can alternatively be placed in an opening, slot and/or pocket in a helmet (e.g., a bicycle, motorcycle, skateboard, football, baseball, hockey, snowboard or ski helmet) or other headwear (e.g., a beanie, a baseball cap or any other type of hat). The sensor pod can include a wireless interface that enables it to communicate with and sync with a bases station, such as a mobile phone, tablet computer, laptop computer, or the like. Exemplary electrical components and modules that can be included within a sensor pod are shown in and described above with reference to FIG. 2. In certain embodiments, the sensor pods are water tight so that they can get wet and still operate.

The foregoing detailed description of the technology herein has been presented for purposes of illustration and description. It is not intended to be exhaustive or to limit the technology to the precise form disclosed. Many modifications and variations are possible in light of the above teaching. The described embodiments were chosen to best explain the principles of the technology and its practical application to thereby enable others skilled in the art to best utilize the technology in various embodiments and with various modifications as are suited to the particular use contemplated. It is intended that the scope of the technology be defined by the claims appended hereto. While various embodiments have been described above, it should be understood that they have been presented by way of example, and not limitation. It will be apparent to persons skilled in the relevant art that various changes in form and detail can be made therein without departing from the spirit and scope of the invention. The breadth and scope of the present technology should not be limited by any of the above-described exemplary embodiments, but should be defined only in accordance with the following claims and their equivalents.

What is claimed is:

1. A sensor module, comprising:
a substrate having a top surface and a bottom surface;
a packaged light source semiconductor device mounted to the top surface of the substrate, the packaged light source semiconductor device including
a light emitter die including one or more light emitting elements encapsulated by a light transmissive molding compound;
a top surface formed by a top surface of the light transmissive molding compound that encapsulates the one or more light emitting elements;
a bottom surface including electrical contacts for the one or more light emitting elements; and
a peripheral surface extending between the top and bottom surfaces;
a packaged light detector semiconductor device mounted to the top surface of the substrate such that there is a gap between the packaged light detector semiconductor device and the packaged light source semiconductor device, the packaged light detector semiconductor device including
    a light detector die including one or more light detecting elements encapsulated by a light transmissive molding compound;
    a top surface formed by a top surface of the light transmissive molding compound that encapsulates the one or more light detecting elements;
    a bottom surface including electrical contacts for the one or more light detecting elements; and
    a peripheral surface extending between the top and bottom surfaces; and
a pre-molded cover structure including a portion of which is molded from an opaque molding compound and also including
    a first pre-molded cavity covered by a first light transmissive window;
    a second pre-molded cavity covered by a second light transmissive window; and
    a barrier formed of the opaque molding compound between the first pre-molded cavity and the second pre-molded cavity;
wherein the pre-molded cover structure is attached to the substrate such that the packaged light source semiconductor device is positioned within the first pre-molded cavity, the packaged light detector semiconductor device is positioned within the second pre-molded cavity, the barrier is positioned between the packaged light detector semiconductor device and the packaged light source semiconductor device, the first light transmissive window covers the one or more light emitting elements of the light emitter die, and the second light transmissive window covers the one or more light detecting elements of the light detector die;
wherein the light transmissive molding compound, which encapsulates the one or more light emitting elements of the light emitter die of the packaged light source semiconductor device, has an index of refraction that is substantially the same as an index of refraction of the first light transmissive window, which covers the first pre-molded cavity of the pre-molded cover structure in which the packaged light source semiconductor device is positioned; and
wherein the light transmissive molding compound, which encapsulates the one or more light detecting elements of the light detector die of the packaged light detector semiconductor device, has an index of refraction that is substantially the same as an index of refraction of the second light transmissive window, which covers the second pre-molded cavity of the pre-molded cover structure in which the packaged light detector semiconductor device is positioned.

2. The sensor module of claim 1, wherein:
the first pre-molded cavity has dimensions that are equal to dimensions of the packaged light source semiconductor device plus a tolerance so that the packaged light source semiconductor device completely fits within the first pre-molded cavity; and
the second pre-molded cavity has dimensions that are equal to dimensions as the packaged light detector semiconductor device plus a tolerance so that the packaged light detector semiconductor device fits within the second pre-molded cavity.

3. The sensor module of claim 1, further comprising:
a further die embedded within the substrate, between the top and bottom surfaces of the substrate, the further die including circuity used to drive the one or more light emitting elements of the light emitter die and/or perform signal processing on a signal produced by the one or more light detecting elements of the light detector die.

4. The sensor module of claim 1, further comprising:
a light transmissive adhesive between the top surface of the packaged light source semiconductor device and the first window, the light transmissive adhesive having an index of refraction that is substantially the same as the index of refraction of the light transmissive molding compound that encapsulates the one or more light emitting elements of the light emitter die and that is substantially the same as an index of refraction of the light transmissive molding compound of which the first window is formed.

5. The sensor module of claim 1, wherein the electrical contacts on the bottom surface of each of the dies are selected from the group consisting of:
    electrically conductive lands;
    electrically conductive pads;
    electrically conductive balls;
    electrically conductive pins; and
    electrically conductive wires.

6. The sensor module of claim 1, further comprising:
one or more additional packaged light detector semiconductor devices mounted to the top surface of the substrate, such that there is a plurality of packaged light detector semiconductor devices mounted to the top surface of the substrate;
wherein the plurality of packaged light detector semiconductor devices and the packaged light source semiconductor device are mounted to the top surface of the substrate such that the packaged light source semiconductor device is positioned in a middle between the plurality of packaged light detector semiconductor devices and such that there is a respective gap between the light source semiconductor device and each of the plurality of packaged light detector semiconductor devices;
wherein the pre-molded cover structure includes one or more additional cavities, each of which is covered by a respective additional window formed of the light transmissive molding compound;
wherein with the pre-molded cover structure attached to the substrate, each of the one or more additional packaged light detector semiconductor devices is positioned within a respective one of the one or more additional cavities in the pre-molded cover structure, and the barrier formed of the opaque molding compound is also positioned between the packaged light detector semiconductor device and the one or more additional packaged light detector semiconductor devices.

7. The sensor module of claim 1, wherein a bottom surface of the substrate includes electrical contacts that enable the sensor module to be electrically connected to further circuitry.

8. The sensor module of claim 1, further comprising a lens that is integrally formed with or attached to one of the first and second windows.

9. The sensor module of claim 1, further comprising:
a packaged temperature sensor semiconductor device mounted to a top surface of the substrate;

a pre-molded temperature sensor cavity within the pre-molded cover structure having dimensions that are equal to dimensions of the packaged temperature sensor semiconductor device plus a tolerance so that the packaged temperature sensor semiconductor device completely fits within the pre-molded temperature sensor cavity; and a metal structure within the pre-molded cover structure that extends between the a top surface of the pre-molded cover structure and a top of the temperature sensor cavity;

wherein the metal structure is made of a thermally conductive metal and provides a thermal coupling between the packaged temperature sensor semiconductor device and a portion of the top surface of the pre-molded cover structure.

10. The sensor module of claim 9, further comprising:
a thermally conductive grease or a thermally conductive adhesive between a top surface of the temperature sensor semiconductor device and a bottom surface of the metal structure.

11. The sensor module of claim 9, further comprising:
one or more electrodes extending upward from a top surface of the substrate;
one or more electrode cavities with the pre-molded cover structure, wherein inner surfaces of the pre-molded cavities are coated with an electrically conductive metal;
one or more metal structures within the pre-molded cover structure each of which extends between the a top surface of the pre-molded cover structure and a top of one of one or more the electrode cavities;
wherein each of the one or more metal structures is made of an electrically conductive metal and provides an electrical coupling between one of the one or more electrodes extending upward from the top surface of the substrate and a respective portion of the top surface of the pre-molded cover structure.

12. The sensor module of claim 11, further comprising:
an electrically conductive grease or an electrically conductive adhesive between a top surface of each of the one or more electrodes and a bottom surface of a respective said metal structure.

13. The sensor module of claim 1, further comprising:
one or more electrodes extending downward from a respective portion of a top surface of the pre-molded cover structure past a bottom surface of the pre-molded cover structure such that a portion of each of the one or more electrodes extend downward from the bottom surface of the pre-molded cover structure;
one or more openings or through holes in the substrate that are configured to receive the portion of the one or more electrodes that extend downward from the bottom surface of the pre-molded cover structure.

14. A user-wearable device, comprising:
a housing having a front side and a back side;
a band that straps the housing to a person's wrist;
a digital display on the front side of the housing; and
a sensor module on the back side of the housing;
wherein the sensor module comprises
a substrate having a top surface and a bottom surface;
a packaged light source semiconductor device mounted to the top surface of the substrate, the packaged light source semiconductor device including
a light emitter die including one or more light emitting elements encapsulated by a light transmissive molding compound;
a top surface formed by a top surface of the light transmissive molding compound that encapsulates the one or more light emitting elements;
a bottom surface including electrical contacts for the one or more light emitting elements; and
a peripheral surface extending between the top and bottom surfaces;
a packaged light detector semiconductor device mounted to the top surface of the substrate such that there is a gap between the packaged light detector semiconductor device and the packaged light source semiconductor device, the packaged light detector semiconductor device including
a light detector die including one or more light detecting elements encapsulated by a light transmissive molding compound;
a top surface formed by a top surface of the light transmissive molding compound that encapsulates the one or more light detecting elements;
a bottom surface including electrical contacts for the one or more light detecting elements; and
a peripheral surface extending between the top and bottom surfaces;
a pre-molded cover structure including a portion of which is molded from an opaque molding compound and also including
a first pre-molded cavity covered by a first light transmissive window;
a second pre-molded cavity covered by a second light transmissive window; and
a barrier formed of the opaque molding compound between the first pre-molded cavity and the second pre-molded cavity;
wherein the pre-molded cover structure is attached to the substrate such that the packaged light source semiconductor device is positioned within the first pre-molded cavity, the packaged light detector semiconductor device is positioned within the second pre-molded cavity, the barrier is positioned between the packaged light detector semiconductor device and the packaged light source semiconductor device, the first light transmissive window covers the one or more light emitting elements of the light emitter die, and the second light transmissive window covers the one or more light detecting elements of the light detector die;
wherein the light transmissive molding compound, which encapsulates the one or more light emitting elements of the light emitter die of the packaged light source semiconductor device, has an index of refraction that is substantially the same as an index of refraction of the first light transmissive window, which covers the first pre-molded cavity of the pre-molded cover structure in which the packaged light source semiconductor device is positioned; and
wherein the light transmissive molding compound, which encapsulates the one or more light detecting elements of the light detector die of the packaged light detector semiconductor device, has an index of refraction that is substantially the same as an index of refraction of the second light transmissive window, which covers the second pre-molded cavity of the pre-molded cover structure in which the packaged light detector semiconductor device is positioned.

15. The user-wearable device of claim 14, wherein the sensor module also includes a further die embedded within the substrate, between the top and bottom surfaces of the substrate, the further die including circuity used to drive the one or more light emitting elements of the light emitter die and/or perform signal processing on a signal produced by the one or more light detecting elements of the light detector die.

16. The user-wearable device of claim 14, further comprising:
- a light transmissive adhesive between the top surface of the packaged light source semiconductor device and the first window, the light transmissive adhesive having an index of refraction that is substantially the same as the index of refraction of the light transmissive molding compound that encapsulates the one or more light emitting elements of the light emitter die and that is substantially the same as an index of refraction of the light transmissive molding compound of which the first window is formed; and
- a light transmissive adhesive between the top surface of the packaged light detector semiconductor device and the second window, the light transmissive adhesive having an index of refraction that is substantially the same as the index of refraction of the light transmissive molding compound that encapsulates the one or more light detecting elements of the light detector die and that is substantially the same as an index of refraction of the light transmissive molding compound of which the second window is formed.

17. The user-wearable device of claim 14, wherein the sensor module also includes
- a packaged temperature sensor semiconductor device mounted to a top surface of the substrate;
- a metal structure within the pre-molded cover structure that extends between the a top surface of the pre-molded cover structure and a top of the temperature sensor cavity;
- wherein the metal structure is made of a thermally conductive metal and provides a thermal coupling between the packaged temperature sensor semiconductor device and a portion of the top surface of the pre-molded cover structure.

18. The user-wearable device of claim 14, wherein the sensor module also includes:
- one or more electrodes extending upward from a top surface of the substrate;
- one or more electrode cavities with the pre-molded cover structure, wherein inner surfaces of the electrode cavities are coated with an electrically conductive metal;
- one or more metal structures within the pre-molded cover structure each of which extends between a top surface of the pre-molded cover structure and a top of one of one or more the electrode cavities;
- wherein each of the one or more metal structures is made of an electrically conductive metal and provides an electrical coupling between one of the one or more electrodes extending upward from the top surface of the substrate and a respective portion of the top surface of the pre-molded cover structure.

19. The user-wearable device of claim 14, wherein the sensor module also includes:
- one or more electrodes extending downward from a respective portion of a top surface of the pre-molded cover structure past a bottom surface of the pre-molded cover structure such that a portion of each of the one or more electrodes extend downward from the bottom surface of the pre-molded cover structure;
- one or more openings or through holes in the substrate that are configured to receive the portion of the one or more electrodes that extend downward from the bottom surface of the pre-molded cover structure.

* * * * *